United States Patent [19]
Lancelot et al.

[11] Patent Number: 5,946,659
[45] Date of Patent: Aug. 31, 1999

[54] SYSTEM AND METHOD FOR NOTIFICATION AND ACCESS OF PATIENT CARE INFORMATION BEING SIMULTANEOUSLY ENTERED

[75] Inventors: Jean F. Lancelot; Jon J. Burford; David S. Gardner, all of San Diego, Calif.

[73] Assignee: Clinicomp International, Inc., San Diego, Calif.

[21] Appl. No.: 08/903,537

[22] Filed: Jul. 30, 1997

Related U.S. Application Data

[63] Continuation-in-part of application No. 08/852,191, May 6, 1997, which is a continuation-in-part of application No. 08/396,004, Feb. 28, 1995, abandoned.

[51] Int. Cl.[6] .................................................. G06F 159/00
[52] U.S. Cl. .................................................. 705/3; 705/2
[58] Field of Search .................................. 707/200, 201, 707/203, 511; 705/2, 3

[56] References Cited

U.S. PATENT DOCUMENTS

| | | | |
|---|---|---|---|
| 4,878,175 | 10/1989 | Norden-Paul et al. | 364/413.01 |
| 4,893,270 | 1/1990 | Beck et al. | 364/900 |
| 4,987,538 | 1/1991 | Johnson et al. | 364/401 |
| 5,001,630 | 3/1991 | Wiltfong | 364/401 |
| 5,033,009 | 7/1991 | Dubnoff | 364/523 |
| 5,065,315 | 11/1991 | Garcia | 364/413.02 |
| 5,072,383 | 12/1991 | Brimm et al. | 364/413.02 |
| 5,077,666 | 12/1991 | Brimm et al. | 364/413.02 |
| 5,121,470 | 6/1992 | Trautman | 395/140 |
| 5,247,611 | 9/1993 | Norden-Paul et al. | 395/161 |
| 5,253,361 | 10/1993 | Thurman et al. | 395/600 |
| 5,253,362 | 10/1993 | Nolan et al. | 395/600 |
| 5,265,010 | 11/1993 | Evans-Paganelli et al. | 364/413.02 |
| 5,301,319 | 4/1994 | Thurman et al. | 395/600 |
| 5,325,293 | 6/1994 | Dorne | 364/413.01 |
| 5,325,478 | 6/1994 | Shelton et al. | 395/148 |
| 5,361,202 | 11/1994 | Doue | 364/413.01 |
| 5,410,704 | 4/1995 | Norden-Paul et al. | 395/700 |
| 5,471,382 | 11/1995 | Tallman et al. | 364/406 |
| 5,473,537 | 12/1995 | Glazer et al. | 364/419.2 |
| 5,517,405 | 5/1996 | McAndrew et al. | 364/401 |
| 5,544,044 | 8/1996 | Leatherman | 364/401 |
| 5,546,580 | 8/1996 | Seliger et al. | 395/600 |
| 5,557,514 | 9/1996 | Seare et al. | 364/401 |
| 5,583,758 | 12/1996 | McIlroy et al. | 395/202 |
| 5,592,945 | 1/1997 | Fiedler | 128/710 |
| 5,594,637 | 1/1997 | Eisenberg et al. | 395/202 |

OTHER PUBLICATIONS

"Patient–focused Eare: Is it for your hospital?" Mary B. Townshed *Nursing Management*, v. 24, n.9. pp. 74–80 Dialog File 15, Acc # 00757395, Sep. 1993.

"The nursing plan: Innovative home health documentation," —C.A. Twardon, et al., *Nursing Management*, v. 24, n. 11, pp. 81–86 Dialog File 15, Acc # 00781 008, Nov. 1993.

"Innovation and Dedication", Kathleen M. Healeys et al. *Hospitals and Health Networks*, v. 66, N .6. , pp. 68–74, Mar. 20, 1994.

*Primary Examiner*—Frantzy Poinvil
*Attorney, Agent, or Firm*—Higgs,Fletcher&Mack LLP; Bernard L. Kleinke

[57] ABSTRACT

A multiple user computerized clinical care system and method of using it, include the use of a group of terminals communicating with a central computer system for sending and receiving patient information for storage and retrieval purposes. The system and method includes managing patient information variance requests, by storing the variance information in the order in which the variance requests are received. The terminals are then supplied with the stored variance information to enable the terminals of the computer system to receive current updated patient information for a given patient substantially concurrently as the updated information is being entered at a plurality of the terminals, without causing any user to wait for the current variance information.

23 Claims, 19 Drawing Sheets

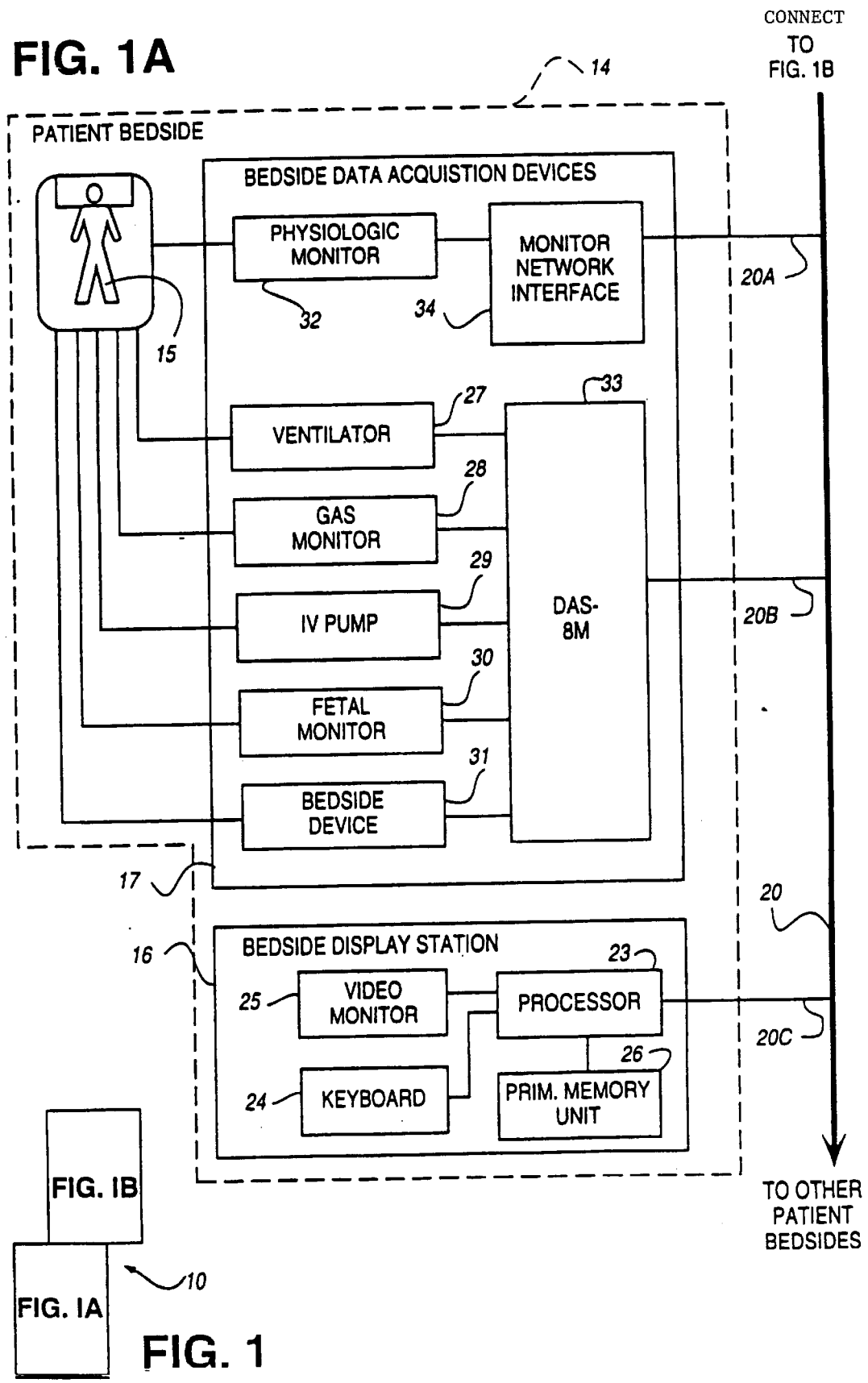

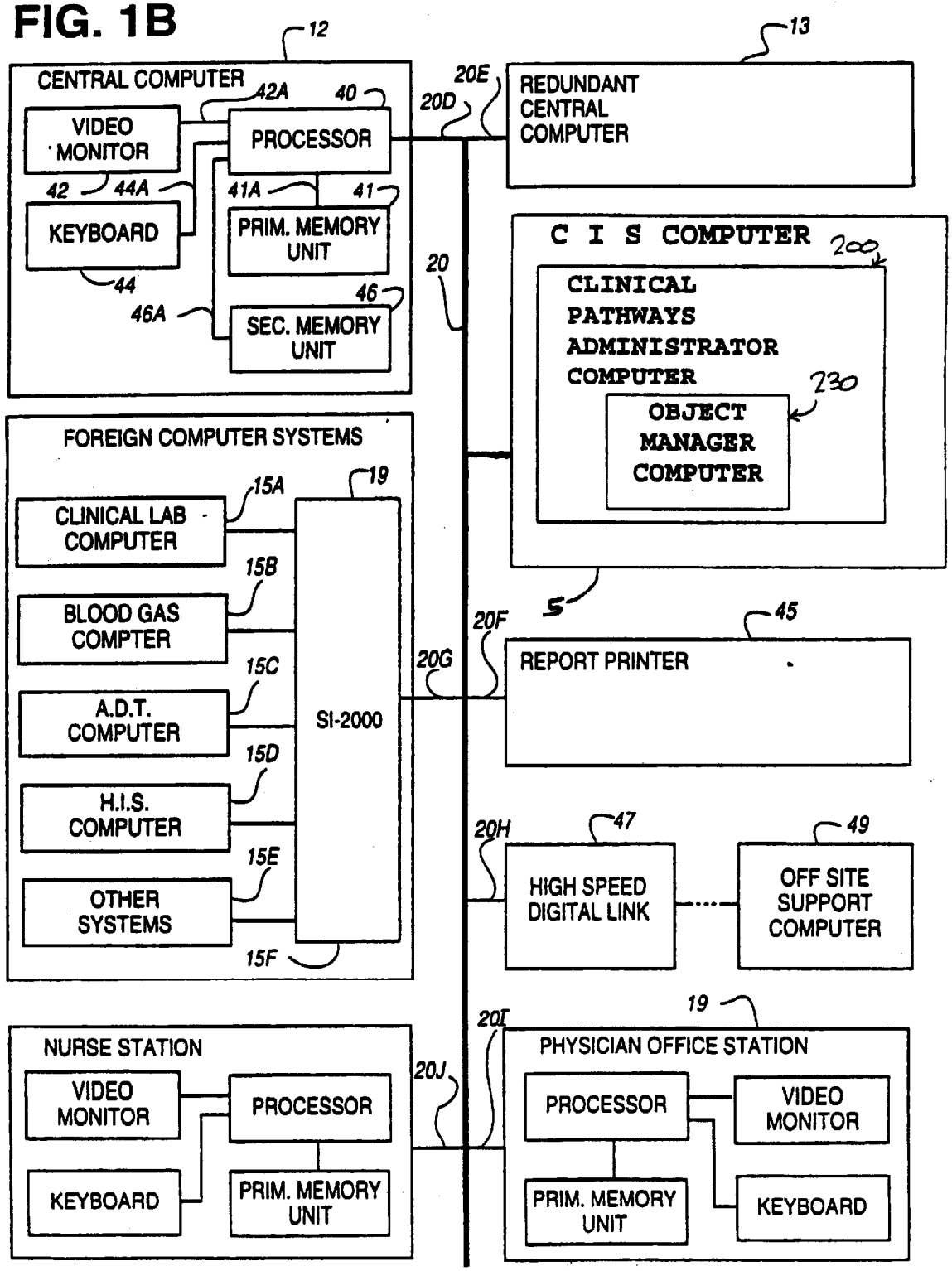

ORDER ENTRY

CATEGORY SELECTION

- MEDICATIONS
- IV DRUGS
- CRYSTALLOIDS
- BLOOD PRODUCTS
- TUBE FEEDINGS
- DIET
- TREATMENTS
- LAB TESTS
- CULTURES
- CONSULTS
- TESTS/DIAG. PROCEDURES
- OUTPUTS
- PT PROBLEMS
- RESUS STAT
- DAILY CHARGES
- ONE TIME CHARGES
- RT TREATMENTS
- STANDARD ORDERS
- VENT ORDERS
- OUTPUTS NO CHC
- IV DRUGS NO CHC
- COLLOIDS
- OTH NO CHC
- OTHER TREATMENTS

ASSIGNED ORDERS — 1010

ORDER EDITING FIELDS

ENTRY [ ]  APPROVAL [ ]  COUNTER [ ]
ORDER TIME [ ]  CATEGORY [ ]  TYPE [ ]
START TIME [ ]  D/C TIME [ ]  ANNOTATION [ ]
CPA NAME [ ]
NAME [ ]
DOSE [ ]
ROUTE [ ]
FREQUENCY [ ]  DELIVER NOW ☐  EXPIRES [ ]
CARRIER [ ]
SITE [ ]
VOLUME ☐(ML)  RATE ☐(ML/HR)  INFUSION ☐(HR)  DRUG WEIGHT ☐(KG)
COMMENT [ ]

| | | | | |
|---|---|---|---|---|
| DRUG NAME | | | | |
| AMOUNT | | | | |
| DOSE | | | | |
| CONCENTRATION | | | | |

ALLERGIES: [ ]

[CANCEL]—1020  [ASSIGN]—1022  [DELIVER NOW]—1024  [ADD IV DRUG]  [DELETE IV DRUG]  [CANCEL ALL]—1026  [DONE]—1028

FIG. 10

ORDER ENTRY

CATEGORY SELECTION
- MEDICATIONS
- IV DRUGS
- CRYSTALLOIDS
- BLOOD PRODUCTS
- TUBE FEEDINGS
- DIET
- TREATMENTS
- LAB TESTS
- CULTURES
- CONSULTS
- TESTS/DIAG. PROCEDURES
- OUTPUTS
- PT PROBLEMS
- RESUS STAT
- DAILY CHARGES
- ONE TIME CHARGES
- RT TREATMENTS
- STANDARD ORDERS
- VENT ORDERS
- OUTPUTS NO CHC
- IV DRUGS NO CHC
- COLLOIDS
- OTH NO CHC
- OTHER TREATMENTS

ASSIGNED ORDERS —1110

ORDER EDITING FIELDS

ENTRY [ ] APPROVAL [ ] COUNTER [ ]
ORDER TIME [ ] CATEGORY [ ] TYPE [ ]
START TIME [ ] D/C TIME [ ] ANNOTATION [ ]
CPA NAME [labwork: SMAG: CIC: PT/PIT: LTA: wit]
NAME [ ]
DOSE [ ]
ROUTE [ ]
FREQUENCY [ ]
CARRIER [ ]
SITE [ ]
VOLUME □(ML) RATE [ ]
COMMENT [ ]
DRUG NAME [ ]
AMOUNT [ ]
DOSE [ ]
CONCENTRATION [ ]
ALLERGIES: [ ]

CHOICE LIST
- DPM
- DPN
- OD
- BIB
- TID
- OIB
- CHS
- OH
- OI
- O2
- O3
- O5

(HR) DRUG WEIGHT □(KG)

[CANCEL] [ASSIGN] [DELIVER NOW] [ADD IV DRUG] [DELETE IV DRUG] [CANCEL ALL] [DONE]
—1120  —1122  —1124      1126—  1128—

| ORDER ENTRY | |
|---|---|
| CATEGORY SELECTION | ASSIGNED ORDERS |

CATEGORY SELECTION:
- MEDICATIONS
- IV DRUGS
- CRYSTALLOIDS
- BLOOD PRODUCTS
- TUBE FEEDINGS
- DIET
- TREATMENTS
- LAB TESTS
- CULTURES
- CONSULTS
- TESTS/DIAG. PROCEDURES
- OUTPUTS
- PT PROBLEMS
- RESUS STAT
- DAILY CHARGES
- ONE TIME CHARGES
- RT TREATMENTS
- STANDARD ORDERS
- VENT ORDERS
- OUTPUTS NO CHC
- IV DRUGS NO CHC
- COLLOIDS
- OTH NO CHC
- OTHER TREATMENTS

ORDER EDITING FIELDS

ENTRY [ ]  APPROVAL [ ]  COUNTER [ ]
ORDER TIME [ ]  CATEGORY [ ]  TYPE [ ]
START TIME [ ]  D/C TIME [ ]  ANNOTATION [ ]
CPA NAME [ ]
NAME [ ]
DOSE [ ]
ROUTE [ ]
FREQUENCY [ ]  DELIVER NOW [ ]  EXPIRES [ ]
CARRIER [ ]
SITE [ ]
VOLUME [ ](ML)  RATE [ ](ML/HR)  INFUSION [ ](HR)  DRUG WEIGHT [ ](KG)
COMMENT [ ]

| DRUG NAME | Dretyltuo | HEHEEii | Hpih | |
|---|---|---|---|---|
| AMOUNT | 2.00(ga) | 500.00(mg) | 2000.00(U) | |
| DOSE | 2.00(mg/al) | 30.00(mg/hr) | 1200.00(U/hr) | |
| CONCENTRATION | 8.00(mg/al) | 2.00(mg/al) | 80.00(U/al) | |

ALLERGIES: [ ]

[CANCEL] [ASSIGN] [DELIVER NOW] [ADD IV DRUG] [DELETE IV DRUG] [CANCEL ALL] [DONE]

CLINICAL PATHWAYS ADMINISTRATOR: WARREN, MITCH

THU JUN 26 14:19

CHEST PAIN R/O MI
- CONSULTS
  - CONSULTS
    - ADMIT-DAY ONE
      - ER-NOTIFY ATTENDING M.D.
      - ER-CALL FOR OLD CHART
      - CASE MANAGER NOTIFIED
      - DEFINE CODE BLUE STATUS

| TESTS | |
|---|---|
| TESTS | |
| ADMIT-DAY ONE | DAY TWO |
| EKG IN ER (12-LEAD) | EKG (12-LEAD) |
| CPK WITH ISOS | CPK WITH ISOS |
| LABWORK: SMAG.CBC.PT/PTT. LDH WIT | CPK WITH MB BANDS RESULTS WITHIN |
| REPEAT CPK WITH ISOS q8H X 3 TOTAL | TREADMILL |
| CXR | |

START TIME — 1320, 1310

↑ 1312   ↑   OK
THU JUN 26   12:13:46   CANCEL
↓ 1314   ↓   CURRENT TIME

TREATMENTS
  TREATMENTS
    ADMIT-DAY ONE

MEDICATIONS
  MEDS
    ADMIT-DAY ONE

DIET
  DIET
    ADMIT-DAY ONE | DAY TWO

ACTIVITY
  ACTIVITY
    ADMIT-DAY ONE | DAY TWO

TEACHING
  TEACHING
    ADMIT-DAY ONE | DAY TWO

13:00:00    19:00:00    FRI JUN 27 01:00

| NOTE TIME: 1:20 27 JUN 1997 | TYPE: TEST CLINICAL VARIANCE NOTE | TOPIC: N/H | MODE: (ENTRY) |

CLINICAL VARIANCE NOTE

CAREPATH [                    ]    SECTION [    ]

TYPE [    ]  | 1 | CABG |            REASON [    ]
             | 2 | LABOR & DELIVERY |
             | 3 | R/O MI |
TREATMENT    | 4 | TONSILLECTOMY |
             | 5 | TOTAL HIP REPLACEMENT |

COMMENT   | 1 |

―1722

F1 NOTES MENUE          F8 STORE

SYSTEM AND METHOD FOR NOTIFICATION AND ACCESS OF PATIENT CARE INFORMATION BEING SIMULTANEOUSLY ENTERED

CROSS-REFERENCE TO RELATED APPLICATIONS

This application is a continuation-in-part patent application of co-pending U.S. patent application Ser. No. 08/852,191, filed May 6, 1997, and entitled "METHOD AND SYSTEM FOR FACILITATING PATIENT CARE PATHS," which is a continuation-in-part patent application of U.S. patent application Ser. No. 08/396,004, filed Feb. 28, 1995, now abandoned and entitled "CLINICAL CRITICAL CARE PATH SYSTEM AND METHOD OF USING SAME," which applications are incorporated herein by reference as if fully set forth herein.

TECHNICAL FIELD

The present invention relates in general to a clinical care system and a method of using it, wherein a multiple number of users can access the system. It more particularly relates to such a method and system for enabling the more efficient and effective communication and charting of patient information relative to patient care for a large number of health care providers.

BACKGROUND ART

Computerized information systems have been employed in health care facilities to assist the health care providers in rendering patient care. In the above-identified co-pending patent application, there is disclosed a system which monitors clinical critical care pathways for patient care. The critical care pathways enable clinical orders and patient progress notes to be efficiently monitored by health care providers.

Clinical orders are entered periodically in computer terminals and the like for each patient by various health care providers such as physicians, nurses, dietitians and pharmacists. The information is then utilized to create patient pathways for the health care providers.

In such systems, there are frequently a large number of different terminals available throughout the health care facility for use by a variety of different health care providers. Should a multiple number of users desire to chart a variance on the same clinical pathway for a given patient, a conflict can arise. If one of the users requests is given priority over the others and the others are then locked out temporarily, an undesirable result occurs. In this regard, the locked out users are forced to wait pending the completion of the variance request by the user given priority. In a modern fast pace clinical care facility where time is of the essence, such delays can be not only inconvenient, but also could adversely affect the welfare of the patient or create undesirable emergency situations for the patient. Another approach could be to have all users attempting to chart on the same patient pathway at the same time, to wait in a queue. However, such an approach is not used, especially for sophisticated multi-disciplined system, where it is important to have current information available to all users at all times.

Yet another approach might be to not lock out any user. However, such an approach is not acceptable and is not used, because of the practical problems arising when entries are being made at the same time by a plurality of users. Without locking, the information would not necessarily be entered properly and incorrect results could occur. Thus, the system integrity could be compromised, and such a result is not acceptable for use by health care providers for patient care.

A further approach could be to save each variance entry, and then perform conflict checking, whereby the first to access would be preferred and permitted to be entered first. This approach is not acceptable, because the remaining users are required to wait, presumably in a queue. Also, determining the priorities for the users may be difficult for some applications.

None of the foregoing approaches are acceptable, because they all create unwanted and undesirable delays in updating patient information, and making it available to other users. Such delays cannot be tolerated in many applications where speed and accuracy are imperative. Proper patient care demands such level of interchange of information among a multi-disciplinary user group.

Thus, it would be highly desirable to have a new and improved computerized clinical care system, which facilitates multiple variance requests occurring simultaneously in the same patient information pathway.

DISCLOSURE OF THE INVENTION

Therefore, the principal object of the present invention is to provide a new and improved multiple user computerized clinical care system and method of using it, wherein a plurality of users can request variances for the same patient pathway simultaneously in a convenient and efficient manner.

Briefly, the above and further objects of the present invention are realized by providing a new and improved multiple user computerized clinical care system and method of using it, wherein multiple users are enabled to chart on the same clinical pathway for a given patient, and yet receive each other's changes simultaneously. For example, if one user on a clinical pathway charts a variance note for an order, then another user viewing the same pathway for the same patient will be made aware of the variance noted by the first user.

A multiple user computerized clinical care system and method of using it, include the use of a group of terminals communicating with a central computer system for sending and receiving patient information for storage and retrieval purposes. The system and method includes managing patient information variance requests, by storing the variance information in the order in which the variance requests are received. The terminals are then supplied with the stored variance information to enable the terminals of the computer system to receive current updated patient information for a given patient substantially concurrently as the updated information is being entered at a plurality of the terminals, without causing any user to wait for the current variance information.

BRIEF DESCRIPTION OF DRAWINGS

The above mentioned and other objects and features of this invention and the method of attaining them will become apparent, and the invention itself will be best understood by reference to the following description of the embodiment of the invention in conjunction with the accompanying drawings, wherein:

FIGS. 1A and 1B, when arranged as indicated in FIG. 1, is a block diagram of a multiple user computerized clinical care system, which is constructed in accordance with the present invention;

FIG. 10 is a new order screen;

FIG. 11 is the new order screen of FIG. 10 with additional orders assigned;

FIG. 12 is the new order screen of FIG. 10 with multiple IV drugs assigned;

FIG. 13 is a clinical pathways administrator screen with a time prompt;

FIG. 17 is a sample variance note;

BEST MODE FOR CARRYING OUT THE INVENTION

Figure 2:
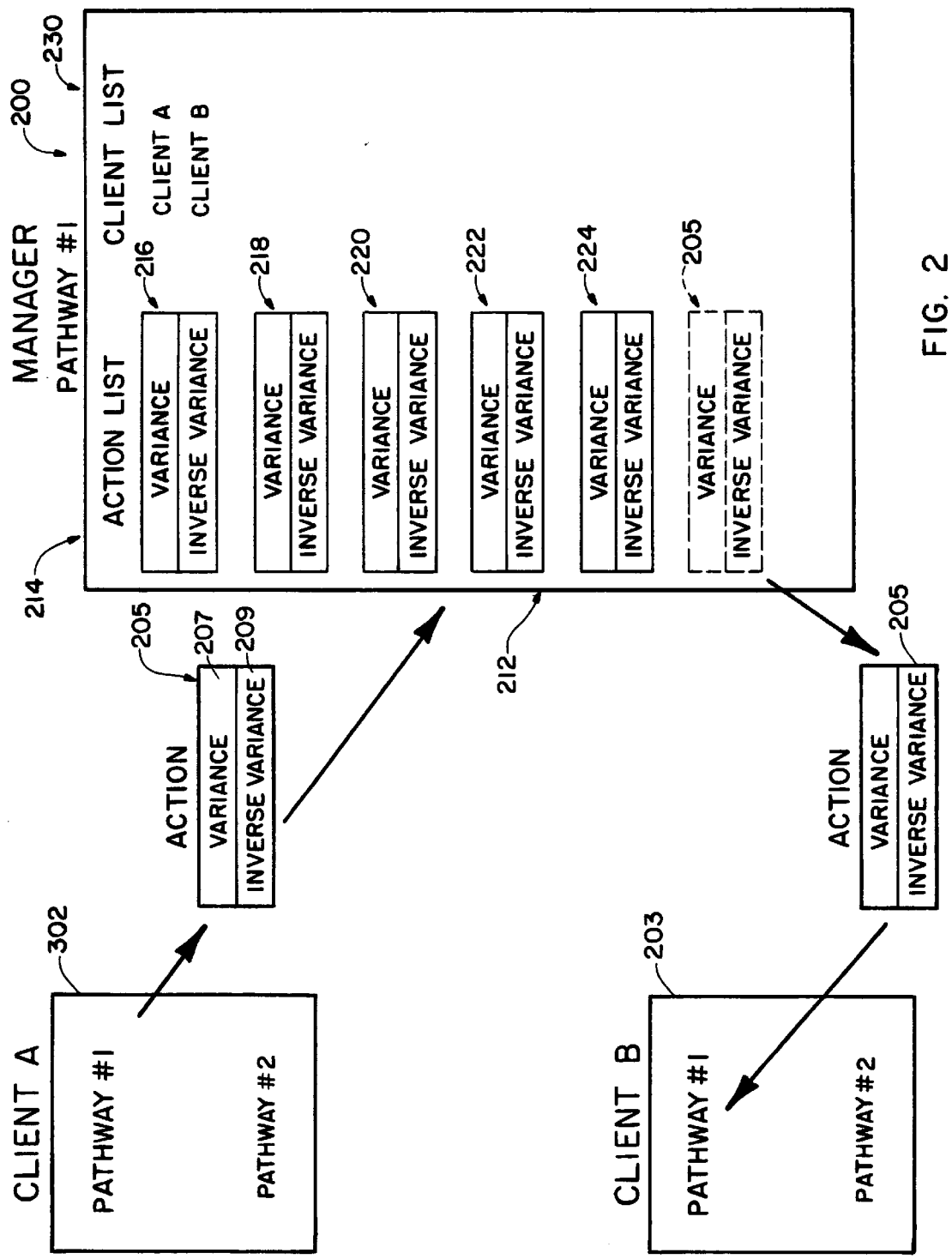
FIG. 2 is a flow chart diagram of the clinical pathways administrator software.

The detailed description is arranged according to the following outline:
A. GENERAL SYSTEM DESCRIPTION
B. GENERAL SYSTEM OPERATION
C. CLINICAL PATHWAYS ADMINISTRATOR SOFTWARE
D. CHARTING A VARIANCE
E. VIEWING A VARIANCE
F. CONCURRENCY

A. GENERAL SYSTEM DESCRIPTION

Referring now to FIG. 1 of the drawings, there is shown a computerized health care facility arrangement 10, which is constructed in accordance with the present invention and which is adapted to generate automatically patient information including critical care flowsheet information for multiple treatment diagnoses, whether medical, surgical or a combination thereof.

The arrangement 10 enables a more efficient and effective communication of the patient information among a group of computer systems within the health care facility arrangement 10. In this regard, a group of patient bedside terminals or locations, such as a bedside location 14 for a patient 15, is used as an order entry computer system utilized by health care providers such as physicians and nurses to enter the patient information such as clinical orders for the patient 15.

According to the invention, a clinical information system 5 (FIG. 1B) having a clinical pathways administrator (CPA) computer 200 retrieves patient information such as clinical orders. The CPA computer 200 includes a plurality of object manager computer such as the computer 230, which encapsulates the retrieved information into an object in object oriented format for sending to one or more of the terminals, as well as to a group of foreign computer systems including terminals, such as a clinical laboratory computer 15A, a blood gas computer 15B, an A.D.T. computer 15C, a hospital information computer 15D, and other systems 15E such as patient admissions computer, patient billing computer and the like. Each one of the foreign computer systems is equipped with its own terminal (not shown) for helping execute application computer software for executing its own specific function.

An individual object manager computer, such as the computer 230 is assigned to each patient pathway.

In accordance with the method of the present invention, the terminals throughout the arrangement 10 are utilized to enter patient information including, for example, patient orders arranged in pathways as explained in greater detail in the foregoing mentioned U.S. patent applications. When the health care provider users request variances to the patient pathway, the variance information is entered via the terminals including the bedside locations, and the foreign computers, to request variances by sending a request message to one of the object manager computers, such as the computer 230, which then retrieves the stored patient information for the appropriate patient in the raw data format. The object manager computer then encapsulates the patient information into an object in object oriented format. The object oriented patient information is then sent to the appropriate computer terminal, requesting the patient information for the patient pathway. Since the information is object oriented information, the computer 15A can readily and conveniently utilize the information as it can be readily interfaced with the application software residing in the foreign computer.

The object variances are then stored by the object manager computer in the order in which the variance requests are received. Each one of the stored variances are sent to the terminals. This entire operation is performed by the CPA computer 5, without delaying any user attempting to chart patient information by entering the variances. Thus, according to the present invention, all current patient information is made available to the users substantially concurrently for the same patient pathway, without creating any substantial delay to the user.

The object manager computer can utilize the Common Object Request Broker Architecture (CORBA) and utilize Interface Definition Language (IDL).

In short, the arrangement 10 facilitates the monitoring of the standard of care of a large number of patients who are confined at various patient bedside locations, such as the patient 15 located at the bedside location 14. Such an arrangement optimizes delivery of care to patients, enables quicker patient recovery, eliminates undesired and unwanted interventions and achieves a more consistent form of care for each patient in a highly efficient manner. Thus, cost savings are realized for the health care provider and desired results are achieved for the patients.

Although the phrase "critical care path" has been employed, it should be understood that other similar phrases can be used. Such phrases include, but are not limited to: "critical path," "care path," and "care map."

The arrangement 10 generally includes a group of patient bedside monitoring locations located through the facility of a health care provider. Such locations would be in an emergency room, an intensive care unit, a cardiac unit, and so forth.

Each patient bedside location, such as the location 14 includes a bedside display station and a group of bedside data acquisition devices, such as bedside display station or terminal 16 and group 17 of bedside data acquisition devices. The display station allows health care providers to observe the patient while entering variance information at bedside while the data acquisition devices facilitate the gathering of patient data and enable health care providers to monitor the condition of a patient at bedside.

In order to facilitate central monitoring, the arrangement 10 also includes a central computer 12 (FIG. 1B) which communicates individually and selectively with the bedside display stations, such as the display station 16.

As will be explained hereinafter in greater detail, the central computer 12 and its associated software gathers and stores patient information, creates flowsheet information, establishes critical care path information for facilitating patient care and to manage the flowsheet information being compiled. The arrangement 10 enables each bedside display station as well as other similar health care provider order entry computers such as a nurse station computer 18, and a physician station computer 19 to access such patient information so health care providers can optimize delivery of care to patients.

The central computer 12 and each bedside patient location display station used for order entry are coupled together via a data bus, such as an ethernet clinical data bus 20. For example, the central computer 12 is coupled to the data bus 20 via a lead or cable 20D, while the bedside display station or terminal 16 is coupled to the bus 20 via a lead or cable 20C. In this manner, a health care provider/user can monitor and enter patient information from many different locations.

In order to provide a more fail-safe and secure operation, the system 10 also includes a redundant central computer 13. An off-site support computer 49 is coupled to the data bus 20 via a high speed data link 47 to provide information to remote locations. A report printer 45 is coupled to the data bus 20 via a lead or cable 20F to enable system users to obtain hard copy reports, flowsheets and other documents for providing efficient patient care.

As best seen in FIG. 1B, the redundant computer 13, the nurse station 18, the physician station 19 and the high speed digital link 47 are coupled to the data bus 20 via leads or cables 20E, 20J, 20I and 20H, respectively.

As best seen in FIG. 1A, the group 17 of bedside data acquisition devices includes a ventilator 27, a gas monitor 28, an IV pump 29, a fetal monitor 30, other monitoring devices, such as a special bedside device 31 and a physiologic monitor 32. The devices 27–31 and 32 are coupled to the data bus 20 via a DAS interface 33 having a lead or cable 20B, and monitor network interface 34 having a lead or cable 20A, respectively.

The system 10 via the central computer 12 is coupled to each group of bedside acquisition devices, such as the group 17 of bedside data acquisition devices for the purpose of monitoring each patient in the health care provider facility. In this regard, the central computer 12 gathers information from the data acquisition devices, receives patient information from various health care providers regarding patient orders and patient diagnoses and, in turn, generates customized critical care path information for each patient. The computer 12 stores the gathered patient information, which can be retrieved by an object manager computer in response to a request message from one of the foreign computers.

As more fully described in the foregoing mentioned co-pending U.S. patent applications, the customized critical care path information is, in turn, utilized by the computer 12 to manage the compiling of flowsheet information for each patient pathway. The flowsheet information is an ongoing compilation of patient information for each patient.

For example, with respect to the group 17 of bedside data acquisition devices, those skilled in the art will understand that as each patient requires customized care, certain ones of the monitoring devices may not be required. Also, which interface device or devices are required, such as the devices 33 and 34, depends on the type of data acquisition devices utilized for monitoring a patient, such as the patient 15. Thus, in accordance with the customized patient information, the arrangement 10 determines that certain rows of the flowsheet of a patient pathway may be unnecessary to cause them to be unused whenever it is determined that a certain bedside data acquisition device is not required for a certain patient. In short then, the critical care path patient information is used by the central computer 12 to manage the flowsheet information causing it to be appropriately compiled for each particular patient being monitored by the arrangement 10. In this manner, a more consistent form of care for each patient is facilitated in a highly efficient process.

Considering now the central computer 12 in greater detail with reference to FIG. 1B, the central computer 12, includes a processor 40 having coupled thereto a primary memory unit 41, such as a random access memory unit, a monitor 42, a keyboard 44 and a secondary memory unit 46, such as a disc drive memory unit. The central computer 12 is generally a super mini-computer, such as sold by Digital Equipment Corporation, Inc. and others. The computer processor 40 is interconnected to the memory unit 41 via a memory cable 41A, the monitor 42 via a video cable 42A, the keyboard 44 via a keyboard cable 44A, and the secondary memory unit 46 via a memory post cable 46A. The primary memory unit 41 and the secondary memory unit 46 contain the long term database information for the critical care path system, and the application software to receive patient data from the bedside display station 16.

The processor 40 and its associated application software performs all the necessary functions of critical care path patient information including 1) retaining clinical information for retrieval and review; 2) performing requested clinical calculations; 3) displaying patient data in tabular and graphic formats; 4) allowing simultaneous multiple user access to any given patient chart information; and 5) integrating patient data acquired from the bedside data acquisition terminals and other acquisition systems such as a clinical laboratory information computer system 15A, a blood gas laboratory computer information system 15B, an A.D.T. (admissions discharges and transfers) computer information system 15C, an H.I.S. (hospital information system) information system 15D, and other foreign systems, such as a foreign computer system 15E.

As best seen in FIG. 1B, an interface unit, such as an SI2000 interface unit 15F, enables such other systems 15A–15E to be coupled to the data bus 20 shared by the central computer 12, the redundant computer 13, and the off-site support computer 49.

Considering now the bedside display station 16 in greater detail with reference to FIG. 1A, the bedside station 16 includes a central processor 23, keyboard 24, video monitor 25 and a primary memory unit 26 such as a random access memory unit. The display station 16 is disposed at the patient bedside location 14 so the health care provider can be in close contact with the patient as information regarding the condition of the patient is entered into the system 10.

The redundant central computer 13 is substantially similar to the central computer 12, and will not be described in greater detail. Those skilled in the art, however, will understand that all of the functions performed by the central computer 12 can also be performed by the redundant computer 13, as well as any other computer system coupled to the network data bus 20 having sufficient speed and secondary memory capability. In this regard, the system 10 has a redundant capability.

B. SYSTEM OPERATION

As noted earlier, the arrangement 10 is a hardware and software system that facilitates the communication of patient information among computer systems. In this regard, the arrangement 10 operates under a master or main program that starts whenever the central computer 12 is activated. In this regard, the arrangement 10 is adapted to be active or ON at all times, since critical care path patient information typically requires twenty-four hour per day, seven day per week monitoring. As all of the system stations can operate independently and simultaneously using the same application software, only the operation of the central computer 12 will be discussed. For clarity purposes in understanding the operation of the arrangement 10, reference may be made from time to time to other stations or data acquisition units.

In operation, and by way of example consider a patient is admitted to a health care facility for a surgical hip replacement procedure. A designated health care provider user utilizing the arrangement 10 via the physician station 19 enters the patients name, the surgical diagnosis and any special orders. The entered information is transferred via the lead or cable 20I to the data bus 20 and thence lead or cable 20D to the central computer 12.

The central computer 12 via the processor 40 causes the information to be processed and stored in the secondary memory unit 46 via the memory port lead 46A. In this regard, the central computer 12 retrieves selectively under user control, critical care path patient information.

After the health care provider/user has tailored the critical care path patient information, the user can cause the information to be stored in the secondary memory unit 46, for subsequent access by support personnel at the bedside of the patient via a display station, such as the display station 16. Such information may also be accessed by the nurse station 18 and the physician office station 19.

When the central computer 12 receives the tailored or customized patient information, the central computer 12 causes customized patient information to be compiled based upon the critical care path information. In this regard, flowsheet information including clinical orders is initially stored in a universal format for displaying many possible patient management information received from the display station 16 and the group 17 of bedside data acquisition devices.

After the patient is at bedside, patient information is gathered by the health care provider/user via the display station 16, and the appropriate bedside devices and then stored in the central computer secondary memory unit 46 for subsequent retrieval by one of the foreign computers in accordance with the present invention. In this regard, the ethernet data bus 20 has common access to each of the systems, computers, and devices via the leads or cables 20A–D and G.

More particularly, a health care provider user or a user of a foreign computer at any time thereafter, can access the stored patient information stored at the central computer 12 via the bedside display station 16, the nurse station 18, and the physician office station 19, as well as via a foreign computer.

From the foregoing, it should be understood that the arrangement 10 facilitates the management of the care of a large group of patients. The management of care is accomplished by creating and storing in the secondary memory unit 46 of central computer 12, patient information including clinical orders, for a large number of different patient diagnoses, both medical and surgical.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

C. CLINICAL PATHWAYS ADMINISTRATOR SOFTWARE

Considering now the Clinical Pathways Administrator software (CPA), this subsystem provides certain functionality for managing pathways and is executed on the computer 200 (FIB.1B). It allows configurable critical pathways for populations based on procedures, diagnoses, and others. It also allows for pathways to be individualized per patient, and generates orders that populate throughout the system 10. The CPA provides time intervals by hours, days, phases, and others. The CPA enables display of more than one clinical pathway, and operates as a real-time application. It provides for the generating of variances when any changes affect: the start time of a section or a row, the end time of a step, the items of a path such as the item name and removing or adding a item, an order including the start time of an order or the discontinuing of an order, the outcome, or the discontinuing or completing of a step outside the expected timeframe as defined by the hospital.

The CPA allows for the generating of variances by individually setting weights per element in a pathway, and provides for user-elected variances on any item of a pathway. The CPA enables the creation and attachment of configurable notes (i.e., patient education notes), and enables the creation and attachment of variance notes describing the variance. The CPA provides for zoom sizing for scalable screen display of main pathway sections down to detailed orders, and provides for easy configuration with drag and drop, copy and paste tools, and others, while being fully mouse driven. The CPA contains configurable color of the screens.

Variance Management Software

Considering now the CPA 200 in greater detail with reference to FIG. 2, the CPA 200 includes a server responsive to requests or changes generated by clients, such as client A 202 and client B 203. The clients 202 and 203 are responsive to the terminals or stations 16, 18 or 19, for example, to facilitate the monitoring and controlling of the patient pathways, such as pathway 1, pathway 2, and pathway 3. Each client is capable of operating on one or more pathways. As shown in FIG. 2, client A 202 is acting on pathway 1 and pathway 2 while client B 203 is acting on pathway 1 and pathway 3, as well as others (not shown).

A request for a change by a client, such as client A 202, in a patient pathway, such as pathway 1, produces an action object 205. Encapsulated within the action object 205 is a variance object 207 corresponding to a variance of the pathway. The action object 205 further includes, and encapsulated there within, an inverse variance object 209 which describes how to undo the requested variance for the particular pathway 1.

An object manager 212 controls the action objects for a particular patient pathway, such as patient pathway 1. The object manager 212 maintains an action list 214 of all action objects for the particular pathway, such as the action objects 205, 216, 218, 220, 222 and 224 for patient pathway 1. The object manager 212 further maintains a client list 230 identifying all clients, such as client A 202 and client B 203, which have opened the particular patient pathway, pathway 1. The action objects 205, 216, 218, 220, 222 and 224 are organized in the action list 214 on a first in first out basis. The object manager 121 is in charge of a single patient pathway, pathway 1, only. Where an object manager, such as object manager 212, does not exist for a particular patient pathway, such as pathway 1, an appropriate object manager will be created.

In operation, the server facilitates passing around changes made to various patient pathways, such as pathway 1. When a patient pathway, such as pathway 1, is opened, the CPA 200 sends a request to the server for the object manager 212 for the pathway 1.

Multiple users can open pathway 1. For example, client A 202 has pathway 1 and pathway 2 opened, while client B 203 has pathway 1 and pathway 3 opened. The object management 212 identifies these users and maintains a current list thereof in the client list 230.

Any change made to a patient's pathway, such as pathway 1, is considered to be a variance of the template pathway. This variance is encapsulated within the variance object 207 that describes the change made and where in the pathway 1 the change was applied. In addition, the inverse variance object 209 is created, wherein the inverse variance object 209 describes how to undo the variance for pathway 1. Both the variance object and the inverse variance object are placed into the action objects 205.

The action object 205 for pathway 1 is then sent to the object manager for pathway 1, object manager 212. The object manager 212 places the action object 205 into the action list 214. The object manager 212 then passes the action object 205 to all of the CPA applications identified in the client list 230. The receiving CPA applications then take the action object 205 and apply it to the respective pathway.

For example, as shown in FIG. 2, client A as indicated at 202 has patient pathway 1 and pathway 2 open. Client A as indicated at 202 generates an action object 205, including variance object 207 and inverse variance object 209, for pathway 1.

The server passes the action object 205 to the object manager 212 for pathway 1. The object manager 212 places the action object 205 in the action list 214 according to when the action object 205 was received. In this regard, the action objects 205, 216, 218, 220, 222 and 224 are maintained in a first in, first out basis to enable the changes made first in time to be acted upon prior to subsequently made changes.

The object manager 212 identifies client A as indicated at 202 and client B as indicated at 203 as currently having pathway 1 opened. Where action object 205 is received first in time with regard to the action objects 216, 218, 220, 222 and 224, the object manager 212 passes the action object 205 to client B as indicated at 203 before the remaining action objects 216, 218, 220, 222 and 224. The client B as indicated at 203 receives the action objects 205 and applies the variance to the pathway 1.

By keeping a list of the actions performed in the object manager 212, it is possible to undo and redo any changes. A user can possibly make several variances and subsequently back the changes out at a later time. The object manager 212 can look up the appropriate action and then change the command to either do or undo for passing the action onto other CPA applications, such as client A as indicated at 202 and client B as indicated at 203.

When a CPA application exits, all necessary object managers, such as object manager 212, remove the CPA application from the client list, such as client list 230. When the object manager client list, such as client list 230, becomes empty, the object manager exits as well.

Clinical Pathways Administrator Functions

Figure 3:
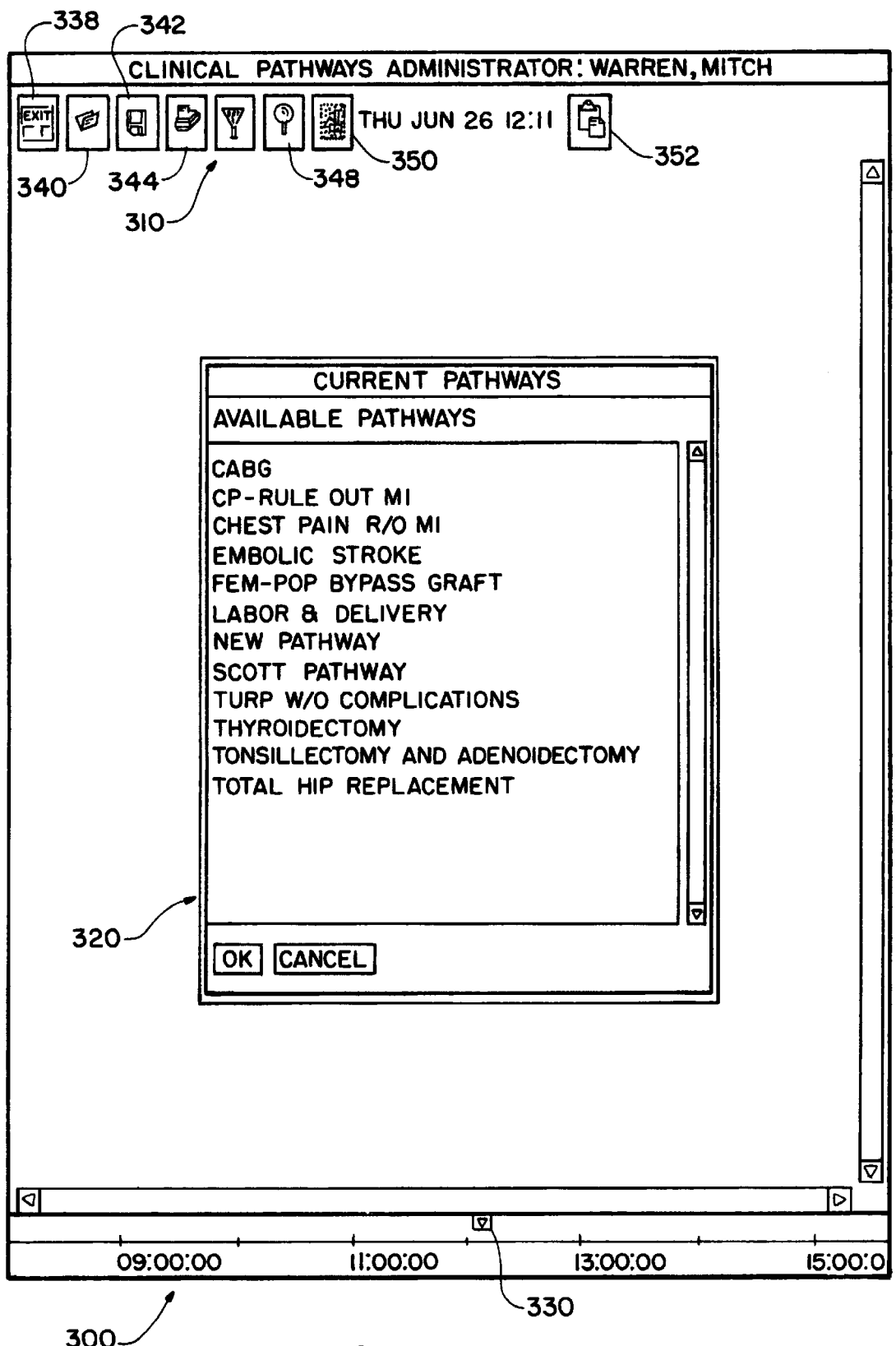
FIG. 3 is a blank clinical pathway administrator screen with an available pathways window.

As shown in FIG. 3, the Clinical Pathway Administrator can be accessed by selecting the soft key for the Clinical Pathway Administrator Screen 300. The blank Clinical Pathways Administrator Screen 300 will appear for the selected patient. Upon accessing the Clinical Pathway Administrator Screen 300, the Tool Bar 310 (a grouping of icons) appears in the upper left corner of the screen. When the cursor is placed on an icon, its function will be described in text below the icon. The icons from left to right are: Exit 338, Open 340, Save 342, Print 344, Filter 346, Zoom 348, Configuration Mode 350 and Clipboard 352. A pathway can be selected from a list of available pathways indicated at 320.

Active Clinical Pathway is a clinical pathway that has been stored and the current time 330 falls between the start and end time of any item within a pathway. Any changes to an active clinical pathway will generate a variance, except for discontinuing an item at the expected timeframe (as defined by the hospital). Annotation is distinguished by an Asterisk (*) and describes any notable event attached to any element in a clinical pathway. Current Time 330 is equal to the current clock time with a minimum resolution of one minute. As time passes, the current time 330 will be updated and the time and the clinical pathway will scroll to the left. Inactive clinical Pathway is one that is saved as inactive and any change to the clinical pathway will not generate a variance. Element Box is the box encircling the label for an item and depicts the duration of an item. The left edge of the box indicates the element's start time. The right edge of the box indicates the End Time. Variance is distinguished by a Dollar Sign ($) and describes any change to an assigned pathway.

The CPA includes several modes operation. Configuration Mode is the mode in which clinical pathways templates can be created or modified. Tailor Mode is the mode in which the clinical pathway has not been assigned to a patient and all changes to the clinical pathway will generate only one variance note. User Mode is the mode in which the clinical pathway has been assigned to a patient and it is either active or inactive.

The pathway is displayed over time. The current time is indicated at the bottom of the screen by an upside down arrow 330. The time to the left of current time 330 is the past; the time to the right of the current time is the future.

Clinical pathway templates are configured by the hospital via the Configuration Mode. The user then opens up a template and "tailors" the template to the patient. To open a clinical pathway template and tailor it as needed for the individual patient, the following steps are performed. Click on the "Open" icon. The Available Pathways window appears displaying existing clinical pathway templates for that environment. Then, 340, and then click on the desired clinical pathway template. More than one clinical pathway can be assigned to a patient and displayed on the screen. Click on the "OK" button, and the selected clinical pathway template appears. The item of detail on the clinical pathway that will be displayed on the screen is configurable per environment.

A Clinical Pathway is a diagnosis or procedural-specific, multi-disciplinary, time-sequenced patient care plan. A Clinical Pathway is started for each patient by assigning a clinical pathway template that has been defined by the hospital per existing protocol. The clinical pathway can be tailored based on the patient's expected progress. Others added to the patient's clinical pathway will be automatically transferred to the appropriate flowsheet and displayed on the Order Entry Screen. A clinician can chart whether the clinical pathway's outcomes were met (completed) or if a change occurred, thus generating a variance note. Variances may be specific to an element or item within a pathway or globally to the pathway. Variances can be initiated individually by the user or automatically by the system 10.

A patient's clinical pathway is presented in elements, each of which is represented on the screen by a unique color. Each color is labeled and visibly indented from the previous element. Each clinical pathway consists of five (5) elements or items of detail. As shown in FIGS. 4–8, the items include pathways, section, now, step and order.

Figure 4:
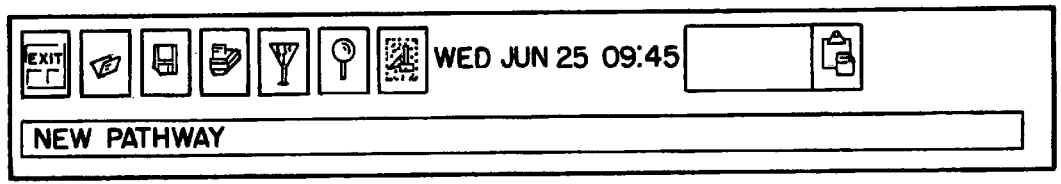
FIG. 4 is a portion of a clinical pathway template screen with a new pathway.

As shown in FIG. 4, typically, when a pathway is selected, only the Pathway item 400 is visible on the screen. More than one clinical pathway can be shown for a patient.

Figure 5:
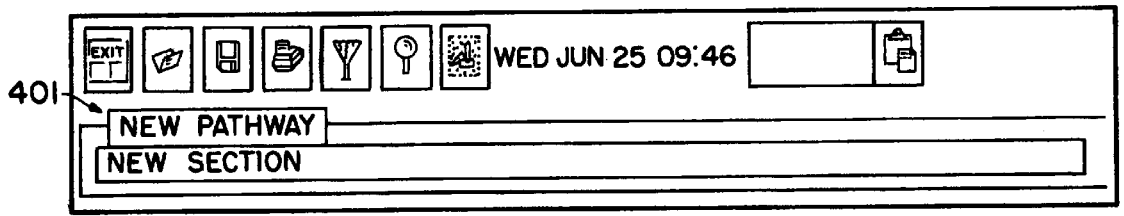
FIG. 5 is a portion of the clinical pathway template screen of FIG. 4 with a new pathway and a new section.

A Section 500 appears below a pathway 401 as shown in FIG. 5. Sections on a clinical pathway may be used to separate different types of charting parameters (i.e., Diagnostic Tests, Diet, Activity).

Figure 6:
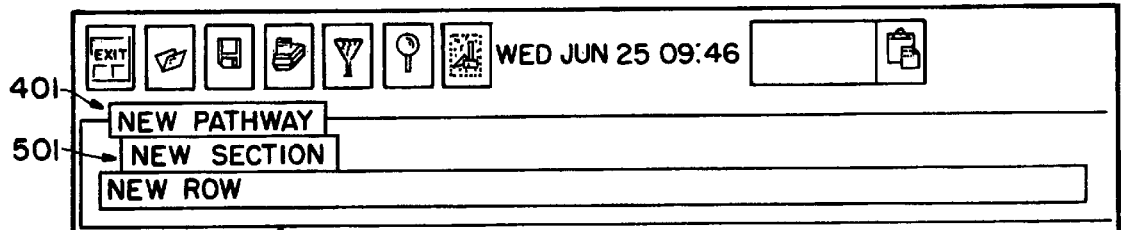
FIG. 6 is a portion of the clinical pathway template screen of FIG. 4 with a new pathway, a new section and a new row.

A Row 600 appears below a section 501 as shown in FIG. 6. Rows may be used to separate the charting parameters (i.e., Labs, Radiology, etc.).

Figure 7:
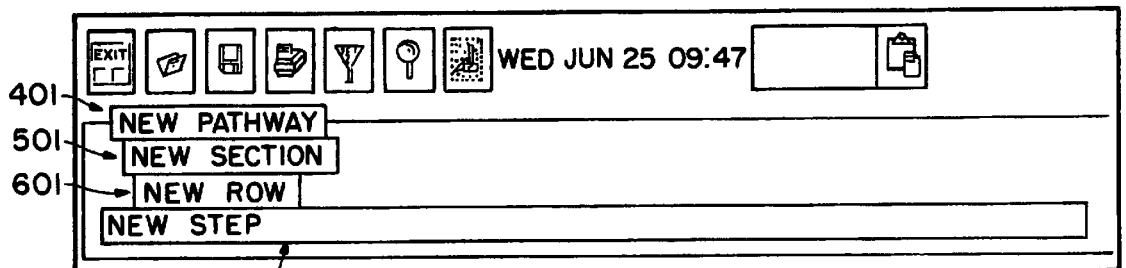
FIG. 7 is a portion of the clinical pathway template screen of FIG. 4 with a new pathway, a new section, a new row and a new step.

As shown in FIG. 7, a Step 700 appears below a row 601. Steps are configured to show an interval of time such as a Phase, a Day, a Stage, etc. Steps for one row are displayed next to each other to visually show the new time interval. The color of the border for a step's box can be configured to indicate if the step is overdue or if the step has been completed.

Figure 8:
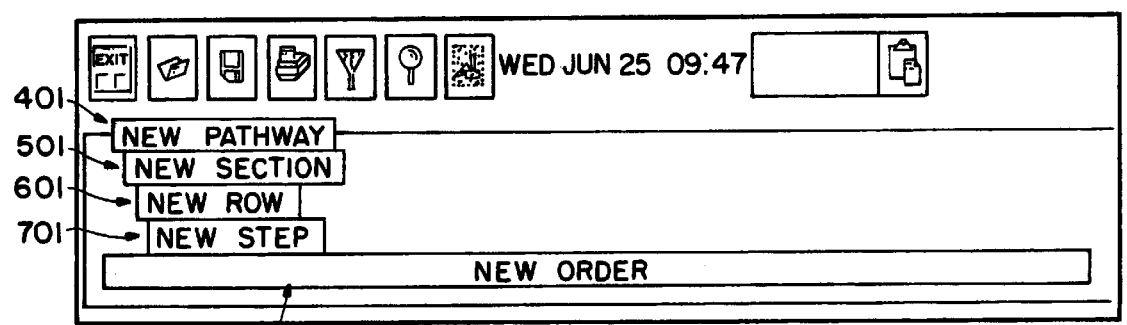
FIG. 8 is a portion of the clinical pathway template screen of FIG. 4 with a new pathway, a new section, a new row, a new step and a new order.

As shown in FIG. 8, an Order 800 appears below a step 701. Orders are assigned via access to the Order Screen and the name of the order appears in the box representing the order.

Figure 9:
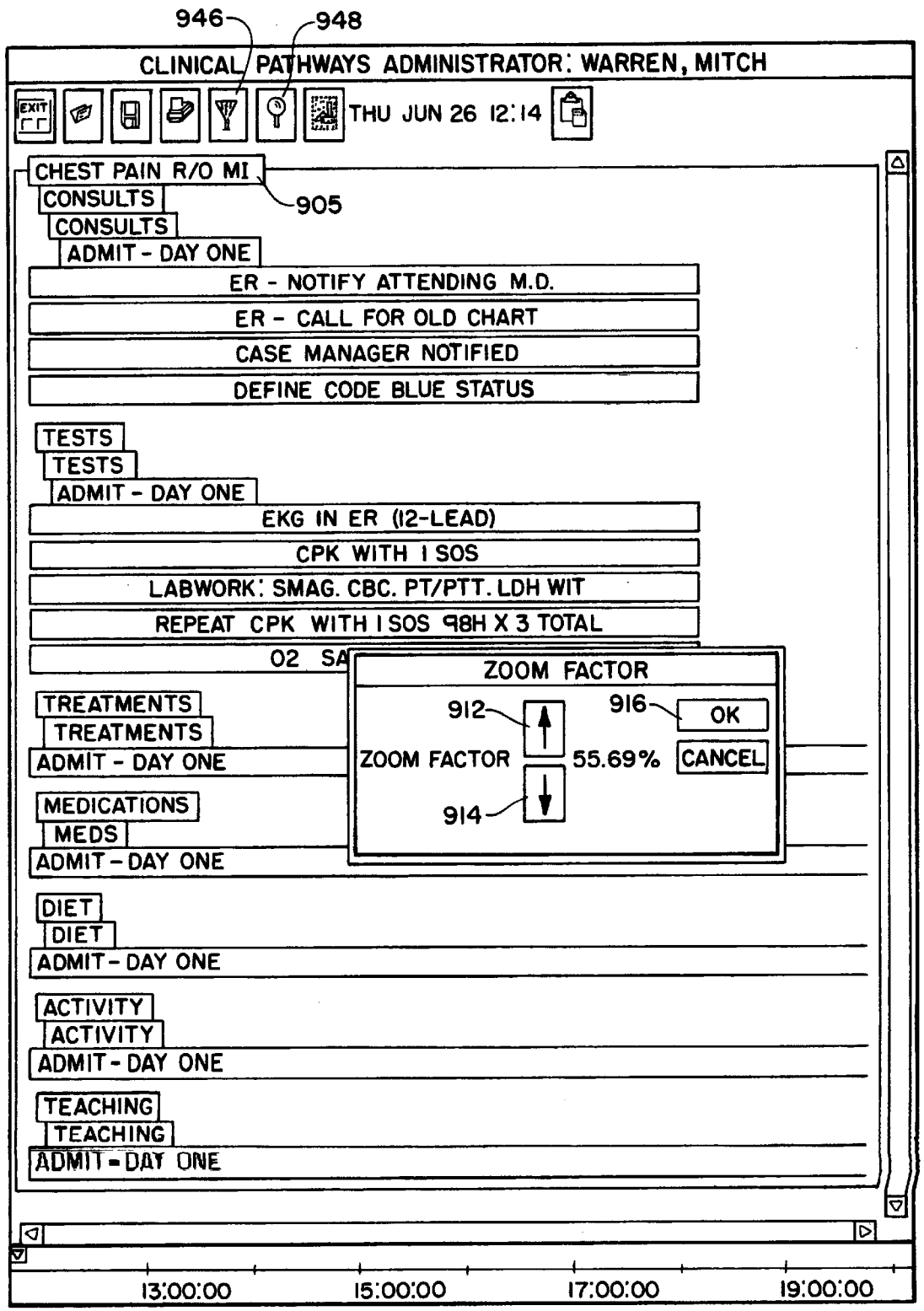
FIG. 9 is a clinical pathways administrator screen with a zoom factor window.

Referring now to FIG. 9, it can be seen that the Clinical Pathways Administrator screen 900 can be scaled to better view the patient's pathways. To change the display size of a pathway 905, the "Zoom" icon 948 is selected. The Zoom Factor window 910 will appear.

Click on the Up Arrow 912 to increase or the Down Arrow 914 to decrease the zoom factor. To save the new display size, click on the "OK" button 916. The pathway 905 will be sized on the screen per the set zoom factor.

To display the clinical pathway in greater detail, to expand an item, hold down the right mouse button and select the desired item. The lower the element on the clinical pathway; the more items will appear. To close an item, hold down the right mouse button and select the item again.

To locate all orders of an order type (i.e., Treatments, Medications, etc.) on a current clinical pathway, perform the following steps. Click on the "Filter" icon 946 (FIG. 9). The Filter Order window (not shown) will appear. Click on one or more order type. Click on the "OK" button. Those items in the pathway(s) that contain the filtered order type(s) will appear on the screen.

To return the display of the pathway to all order types, deselect all selected order types in the Filter Orders window and click on the "OK" button.

The user can change the patient's future orders, the start time for all items in a clinical pathway except for a step item and the end time for a step item. Orders on the CPA are distinguished as either Future or Current orders. Future Orders—Orders assigned on the clinical pathway and not stored to a patient can be deleted or edited; however, changes to the order will generate a variance. Current Orders—Orders assigned and saved on the clinical pathway can be viewed and only the D/C Time can be changed. When the time moves the clinical pathway to the next step in which future orders will need to become current orders, the user will be prompted to store the orders.

To create a new order to a pathway, move the cursor to the Step where the New Order will reside. Hold down the right mouse button. Click on the New Order option. The Order Screen 1000 will appear (FIG. 10).

Select an order category from a Category Selection window 1010 by double clicking. The selected order category will appear on the screen 1010. Fields not applicable to the selected category will be "grayed" out.

Enter in the desired information. To exit from the category selected and clear all fields on the screen, click on another order category or click on the "Cancel" button 1020. The cursor can be moved in the Order Entry Screen 1000 with the keyboard [Tab] and the [Shift] keys. The [Tab] key moves the cursor forward to the next field. The [Shift] [Tab] key moves the cursor backward to the previous field. Type in your data in free text and press the [Enter] key; OR click once on the desired choice list item in the choice list and press the [Enter] key; OR click twice on the desired choice list item in the choice list. A "filter" field for choice list items is available at the top of the choice list window and will display choice list items that match the text typed in the filter field.

The order must contain Order Time and Name for the order to be accepted. For IV Drugs and Medications, the Dose must be also entered.

When finished with entering the new order, click on either the "Assign" button 1022 to assign the order and enter in additional orders or click on the "Done" button 1028 to assign the order and return to the clinical pathway. If the "Assign" button 1022 is selected, the cursor will appear in the Category Selection window 1010 and the edited order will appear in the "Orders Assigned So Far" window 1040. Depending upon the user permission level, when the order is stored the asterisks at the top of the screen will be replaced by the initials of the user. A Notes Menu Screen 1600 (FIG. 16) will appear for the entry of a variance note, and will be described hereinafter in greater detail.

The Start Time for orders are determined on the clinical pathway. Orders can also be added by dragging and dropping another order.

To edit the unstored order, click on the Edit Order option on the desired order item with the right mouse button. The Edit prompt will appear. Type in "Y" for Yes and press the

[Enter] key. The Order Entry Screen will appear. Click on the field to be edited. Enter in the desired changes in the available fields per the category type.

To edit an approved order, you must have the appropriate Edit Level approval permission. The status of the order will determine which parameters of the order may be changed. There are three (3) edit permission levels: If the order has NOT been stored (the asterisks (***) are visible), all parameters can be edited. If the order has been stored, yet not approved, all parameters except for the Order Time can be edited. If the order has been stored and approved, only the Stop Time can be changed. If the order has expired, the order will need to be reordered.

When finished with editing the order, click on either the "Assign" button 1022 to assign the order and enter in additional orders or click on the "Done" button 1028 assign the order and return to the clinical pathway. Depending upon the user permission level, when the order is stored the asterisks at the top of the screen will be replaced by the initials of the user. The Notes Menu Screen 1600 (FIG. 16) will appear for the entry of a variance note.

To assign additional orders while in the Order Entry Screen, 1100 (FIG. 11) select an order category from the Category Selection window 1110 by double clicking on the desired order category as shown in FIG. 11. The selected order category will appear on the screen 1100. Fields not applicable to the selected category will be "grayed" out. To exit from the category selected and clear all fields on the screen, click on another order category or click on the "Cancel" button 1120.

Enter in the requested information in the available fields per the category type. When entering an order with a frequency of X1, STAT, or PRN, then the order can be delivered upon ordering via the "Delivery Now" button 1124.

When finished with entering the new order information and to enter another order, click on the "Assign" button 1122. The assigned order will move to the "Orders Assigned So Far" window 1140 and the cursor will be positioned in the Category Selection window 1110. To abort the current, assigned order and return to the pathway, click on the "Cancel All" button 1126. When finished with entering the needed orders, click on the "Done" button 1128.

Assigning an intake field is synonymous with hanging a bag of fluid. Once a fluid has been assigned, the hourly infusion can be charted. An Intake Fluid order must include the Name, Site, Volume, Rate and Order Time for assignment. The assigned and stored intake fluid volume will NOT appear on the balance sheet to the right of the Intake and Output flowsheet. Only the charted infusion total is tallied per shift.

IV Drugs will appear on the Vital Signs Flowsheet for charting drip rates and on the Medications Flowsheet for medications tracking. When the drug is selected, the default carrier fluid will be automatically added to the IV Drug. When entered, the IV Drug order's fields will default to the current hospital standard These default standards (i.e., Amount, Dose, Concentration) can be edited by typing in the new values. The standard will continue to be displayed on the Order Entry screen for reference. When the drug amount and/or concentration is changed, the other fluid standards will automatically adjust. When ordering an IV Drug, the unit of time for the IV Drug dose includes x/day (e.g. 24 hr). These phrases for the time of measure (e.g., min., hr., day) for the IV Drug dose is configurable. For example, "day" can be configured as 24 hr, 24 h, day, etc.

An Order Entry Screen 1200 for assigning multiple IV drugs is shown in FIG. 12. Once the first IV Drug and fluid is entered on the Order Entry Screen 1200, additional IV Drugs may be added by clicking on the "Add IV Drug" button 1230. The first IV Drug carrier will NOT change even if the additional drugs have different default carriers. To delete the IV drug the cursor is on, click on the "Delete IV Drug" button 1232. The remaining IV drugs may move to the left to fill in any empty fields. If the Fluid volume or rate is changed, it will recalculate the concentration and dose for ALL drugs in this fluid.

When an IV Drug amount is entered, it will only calculate the corresponding dose and concentration. If a dose is changed, it will change the rate for all fluids in the order If the rate is changed, the system will automatically recalculate all of the doses. If a concentration is changed, it will only change the corresponding amount and dose. The final multiple IV drug name will be carrier+ivdrug1+ivdrug2+. . . . When assigned and stored, each additional IV drug will create an extra row in the display of the multiple IV drug on the I&O, Medications and Vital Signs flowsheets as shown below.

At a minimum, the medication and dosage fields must be entered for the medication order to be assigned. Medication expiration times are configurable per medication. Time markers will automatically appear on the flowsheet for pre-set frequency schedules (i.e., BID, TID, QID). Time markers will automatically appear on the flowsheet for delayed frequency schedules after the administration of the first dose.

Whenever a future order is deleted in the user mode, a variance is automatically generated. To delete a future order, move the cursor to the order to be deleted. Hold down the right mouse button. Click on the Delete option. The selected order will be removed. The Notes Menu screen 1600 (FIG. 16) will appear for the entry of a variance note. All times for all future elements of a clinical pathway can be adjusted via a mouse drag.

To assign the Start Time for a Pathway, Section or Row in the Clinical Pathways Administrator Screen 1300 as shown in FIG. 13, move the cursor to the desired item. Hold down the right mouse button. Click on the Time option. A Time window 1310 appears when creating a start time or changing the start time. The Time window 1310 allows the day and the time in hours and minutes to be modified.

Click on the "Up Arrow" or "Down Arrow" 1314 button. The "Up Arrow" button 1312 adds a day to the date and an hour to the time. The "Down Arrow" button 1314 subtracts a day to the date and an hour to time. Click on the "OK" button 1320. The left edge of the box for the selected item will be moved to the entered Start Time. The Notes Menu screen 1600 (FIG. 16) will appear for entering a variance note.

The Start Time for an order can be assigned via the Edit function or by dragging the order box while holding down the Left Mouse button.

To assign the Start Time for an Order, move the cursor over the desired edge of the order box to be changed. Hold down the Left mouse button and drag the order box to the desired time. Let go of the Left mouse button when at the desired time. The selected order will appear at the new Start Time. The Notes Menu screen 1600 (FIG. 16) will appear for entering a variance note.

All orders in a step will end at the step's end time. The step's end time can be changed by either changing the end time or changing the next step's start time. To modify the end time for a step, move the cursor over the right edge of the step's box to be changed. Hold down the Left mouse button and drag the step's box to the desired End Time. Let go of the Left moues button when at the desired time. The selected step will appear at the new End Time. The Notes Menu screen 1600 (FIG. 16) will appear for entering a variance note.

Once a clinical pathway has been assigned for a patient, the user can then: chart an annotation on the patient's status; or chart a variance; or complete the outcome for an item has been met. The Store Order prompt appears for the user to store any orders that have become newly active on the clinical pathway based on the current time To note circumstances surrounding a patient's status on a clinical pathway, move the cursor to the desired item. Hold down the right mouse button. Click on the Chart Annotation option. The Notes Menu for entering an annotation will appear.

Click on the desired note. The Note Time window will appear. If the note is a time note and the pathway already contains one, a prompt will appear to select another note. Enter the time. The selected note will appear. Enter the requested note information. When completed with entering the note, click on the "Store" soft key <F8>. Enter an ID code. To return to the Clinical Pathway Administrator Screen, click on the "Exit Note" soft key <F1>.

Figure 14:
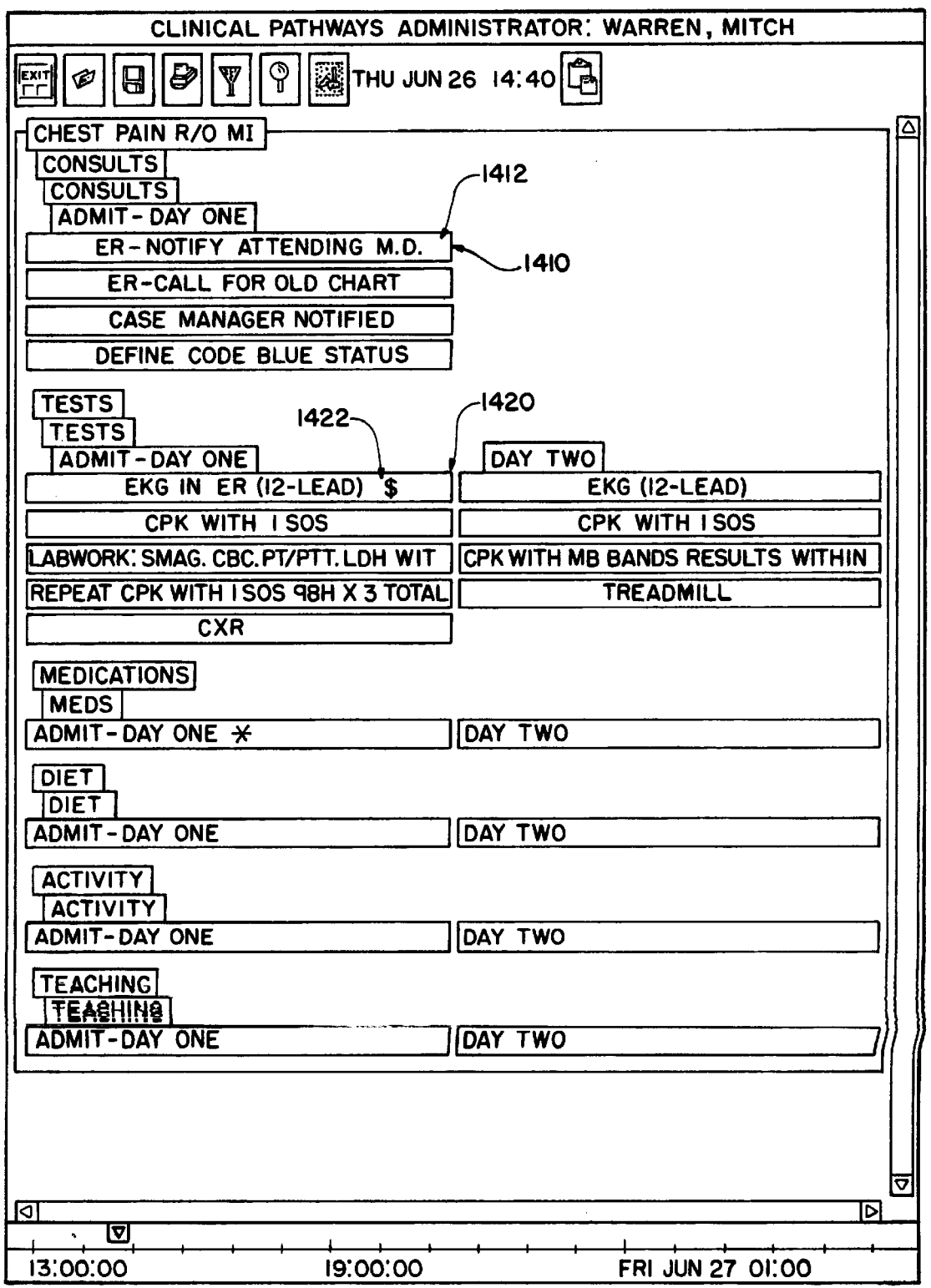
FIG. 14 is a clinical pathways administrator screen with a highlighted annotation.

An element 1410 with an annotation is depicted with an Asterisk (*) 1412 in the element box as shown in FIG. 14. To view any annotation on a patient's clinical pathway, move the cursor to the desired item box. Hold down the right mouse button. Click on the View Annotations option. The Notes Menu screen 1600 (FIG. 16) will appear with a patient's annotations for only the item listed.

Click on the desired annotation. Click on the "Review Note" soft key <F2> 1624 to view the annotation. Click on the "Note Menu" soft key <F1> to return to the Notes Menu Screen. When completed with viewing a patient's annotation, click on the "Exit" soft key <F1> 1622.

D. CHARTING A VARIANCE

Any change to an active clinical pathway generates either a system-forced or elective variance. Variances to the clinical pathway requires the clinician to chart a variance. The type of variance charted by the clinician depends upon the Variance Note selected. The health care facility is responsible for configuring variance notes for individual or global variance. Once a variance is charted, the pathway displays the variance. To chart a variance, the cursor is moved to the desired item. The right mouse button (not shown) is held down. Click on the Chart Variance option. The Variance Note menu will appear. Click on the desired variance note. The Note Time window will appear. If the variance note is a timed note and the clinical pathway already contains one, a prompt will appear to select another note. Enter the time. The selected variance note 1700 (FIG. 17) will appear. Enter the requested variance note information. When completed with entering the variance note, click on the "Store" soft key (not shown) or <F8>. The user then enters his or her ID code. To return to the Clinical Pathway Administrator Screen, the user clicks on the "Exit Notes" soft key <F1>.

E. VIEWING A VARIANCE

An item 1420 with a variance is depicted with a Dollar Sign ($) as indicated at 1422 in FIG. 14, in the element box. The Dollar Sign indicia is generated as part of the charting procedure to alert the users to the existence of a variance in this pathway.

Figure 15:
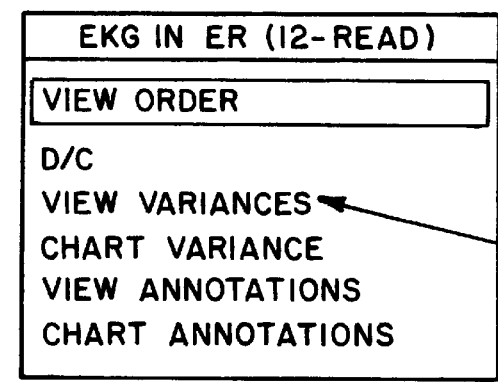
FIG. 15 is a pop-up window for a particular item on a patient clinical pathway.

To view the variances on a patient's clinical pathway, the cursor is moved to the desired item. Thereafter, the right mouse button is held down. As shown in FIG. 15, the screen 1500 appears. The View Variances option is then selected by clicking on it.

Figure 16:
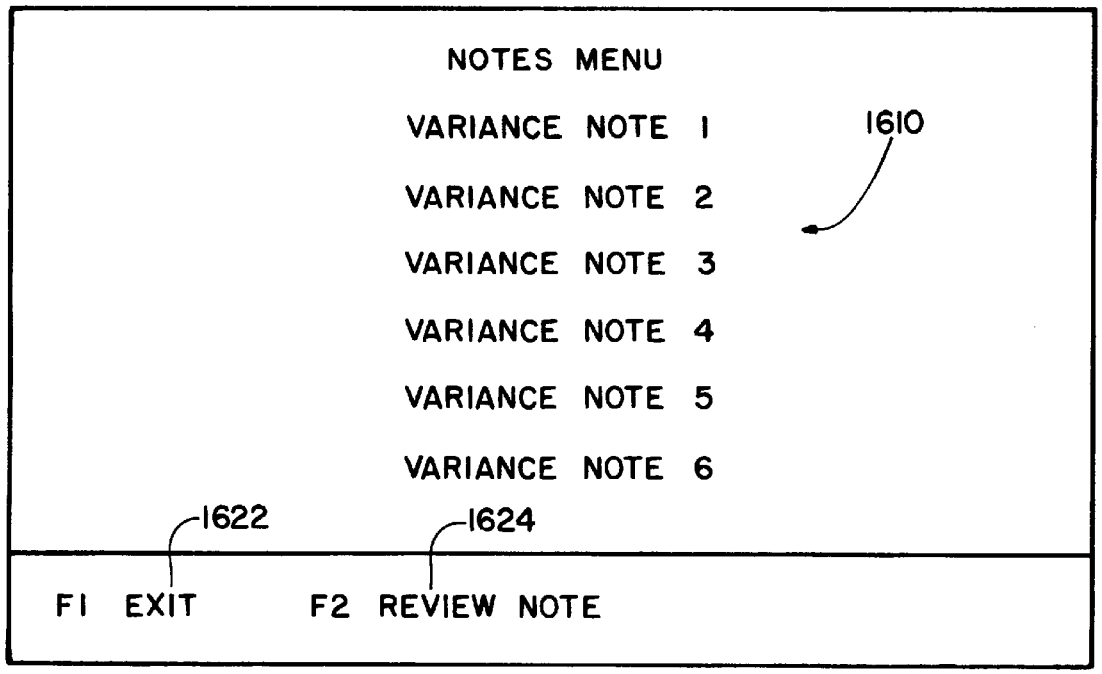
FIG. 16 is a notes menu screen.

As shown in FIG. 16, a pop-up Notes Menu screen 1600 appears with a patient's variances only for that item listed. The desired variance is selected by clicking on it.

Click on the "Review Note" soft key (not shown) or <F2> as indicated at 1624 (FIG. 16) to view the variance. The screen 1700 of FIG. 17 appears to provide a description of the variance. Click on the "Notes Menu" soft key (not shown or <F1> as indicated at 1722 to return to the Notes Menu Screen. Thereafter, another variance can be selected in a similar manner. When the viewing of a patient's variances is completed, click on the "Exit" soft key (not shown) or <F1> as indicated at 1622.

Editing a current, active clinical pathway will automatically generate a variance. To discontinue an item, move the cursor to the desired item. Hold down the right mouse button. Click on the D/C option. A D/C Confirmation prompt will appear.

Figure 18:
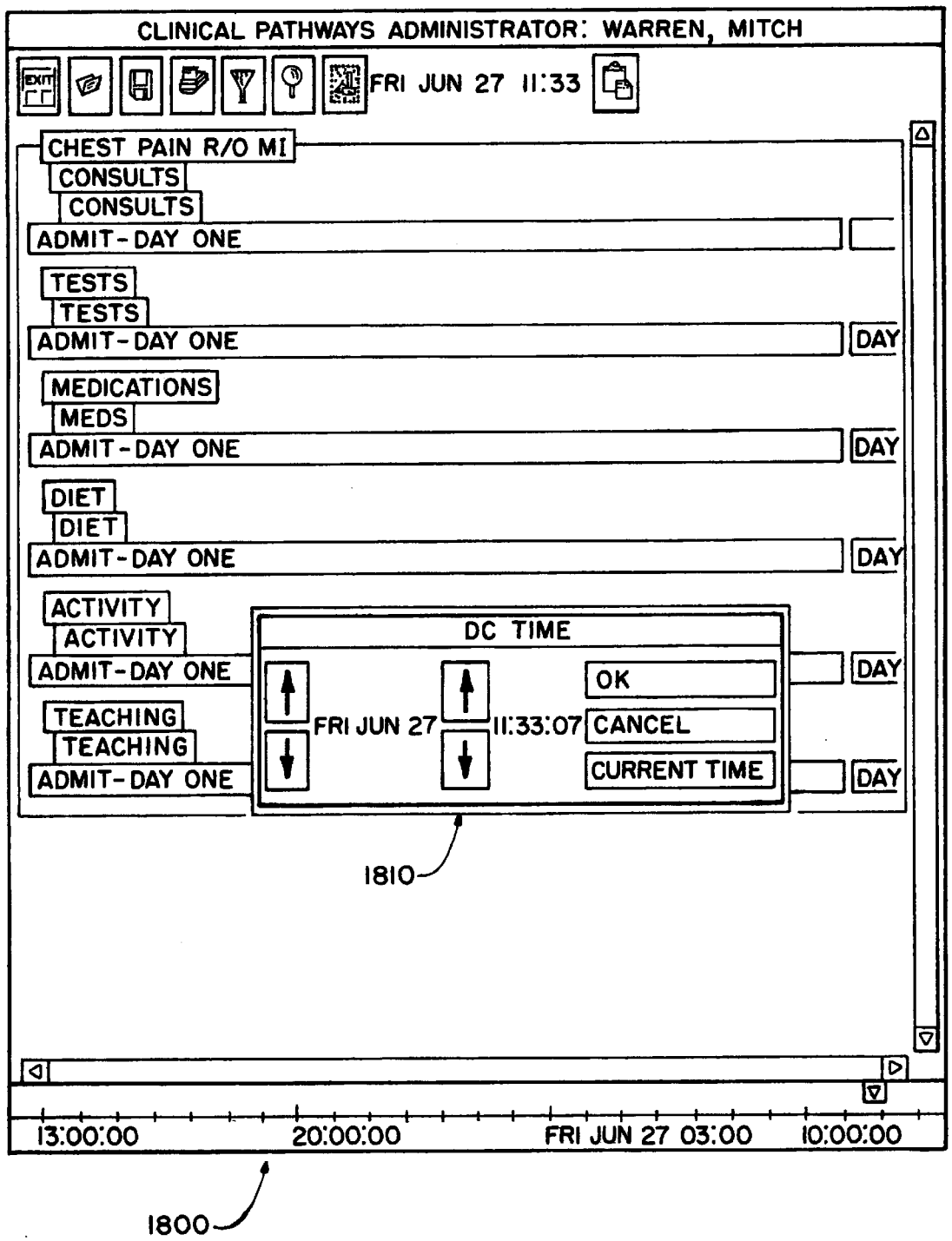
FIG. 18 is a clinical pathways administrator screen with a DC window.

Click on the "OK" button. The D/C Time window 1810 will appear as shown in FIG. 18. Enter the desired D/C Time. The Notes Menu screen will appear for the entry of a variance note.

Figure 19:
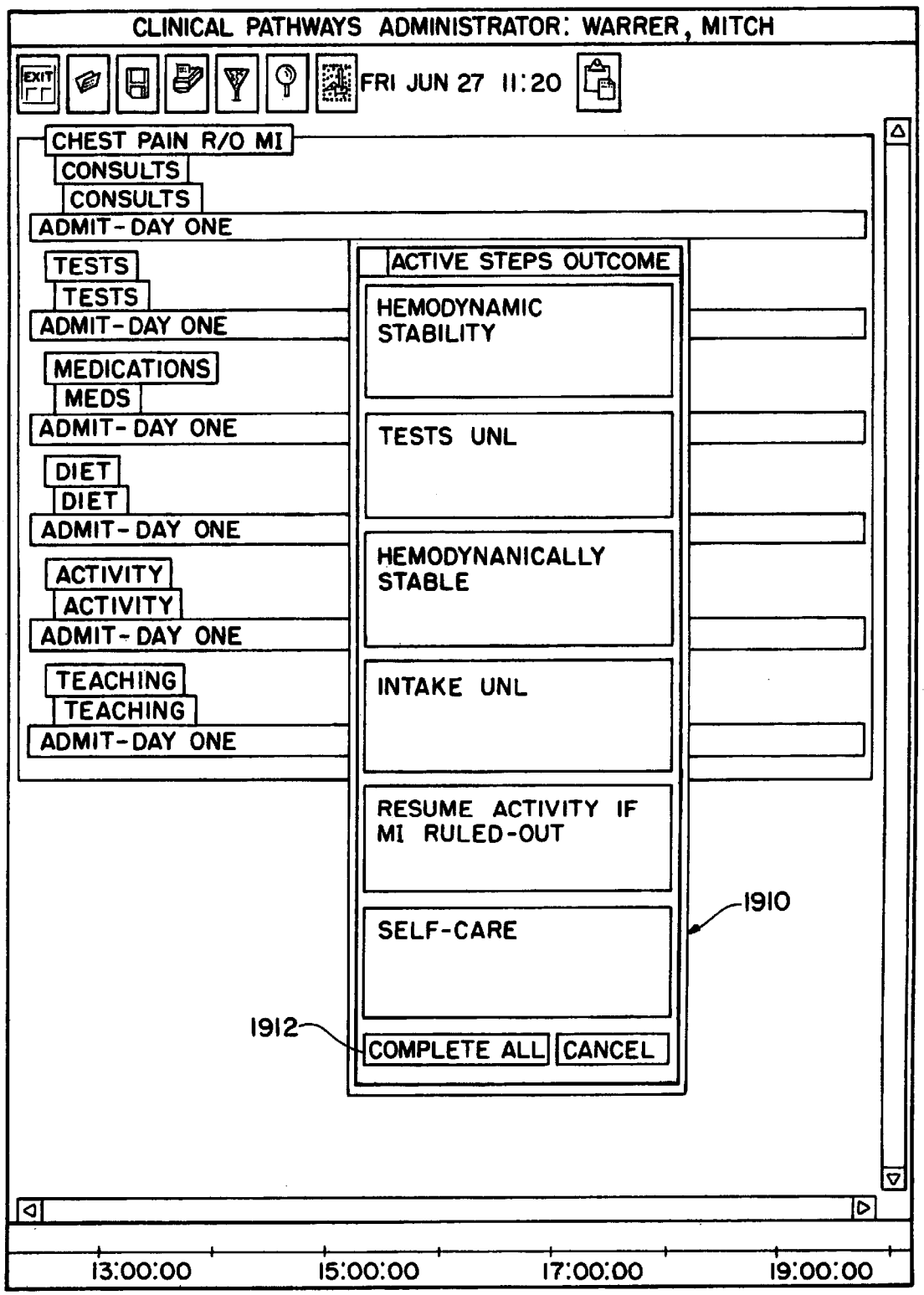
FIG. 19 is a clinical pathways administrator screen with a step outcome window.

When the patient progresses to the next step, the clinician can document that the outcomes have been met for that step and discontinue to the next step. By selecting the Step Outcome at the pathway level as shown in FIG. 19, the user can view the expected outcome with the option to discontinue that step. To record the completion of an entire, active steps' outcome, move the cursor to the pathway item. Hold down the right mouse button. Click on the Step Outcome option. All active outcomes for the step will appear in the Outcome window 1910.

Click on the "Complete All" button 1912. Enter in ID code to approve orders for the patient contained in the next step. The D/C Time window will appear. Enter the desired D/C Time. The step will be discontinued at the time entered.

To record the outcome completion for an individual, active step, move the cursor to the desired step. Hold down the right mouse button. Click on the Outcome option.

To complete the step without viewing the outcomes, click on the "Complete" option. The outcomes for that individual, active step will appear in the Outcome window.

Click on the "Outcome Met" button. Enter in ID code to approve orders for the patient contained in the next step. The D/C Time window will appear. Enter the desired D/C Time. The step will be discontinued at the time entered.

To view an order, move the cursor to the desired order box. Hold down the right mouse button. Click on the right mouse button. Click on the View Order option. The Order Screen will appear. When completed with viewing the order, click on the "Exit" button.

If an order is discontinued outside the expected time (configured time window), then a variance will be automatically generated. To discontinue a current order, move the cursor to the order to be discontinued or deleted. Hold down the right mouse button. Click on the D/C option. The D/C Time window will appear.

Enter the desired D/C Time. If the D/C time is within the configured time window of the expected time, then the order will be discontinued. If the D/C time is outside the configured time window of the expected time, then the Notes Menu screen will appear for the entry of a variance note.

Figure 20:
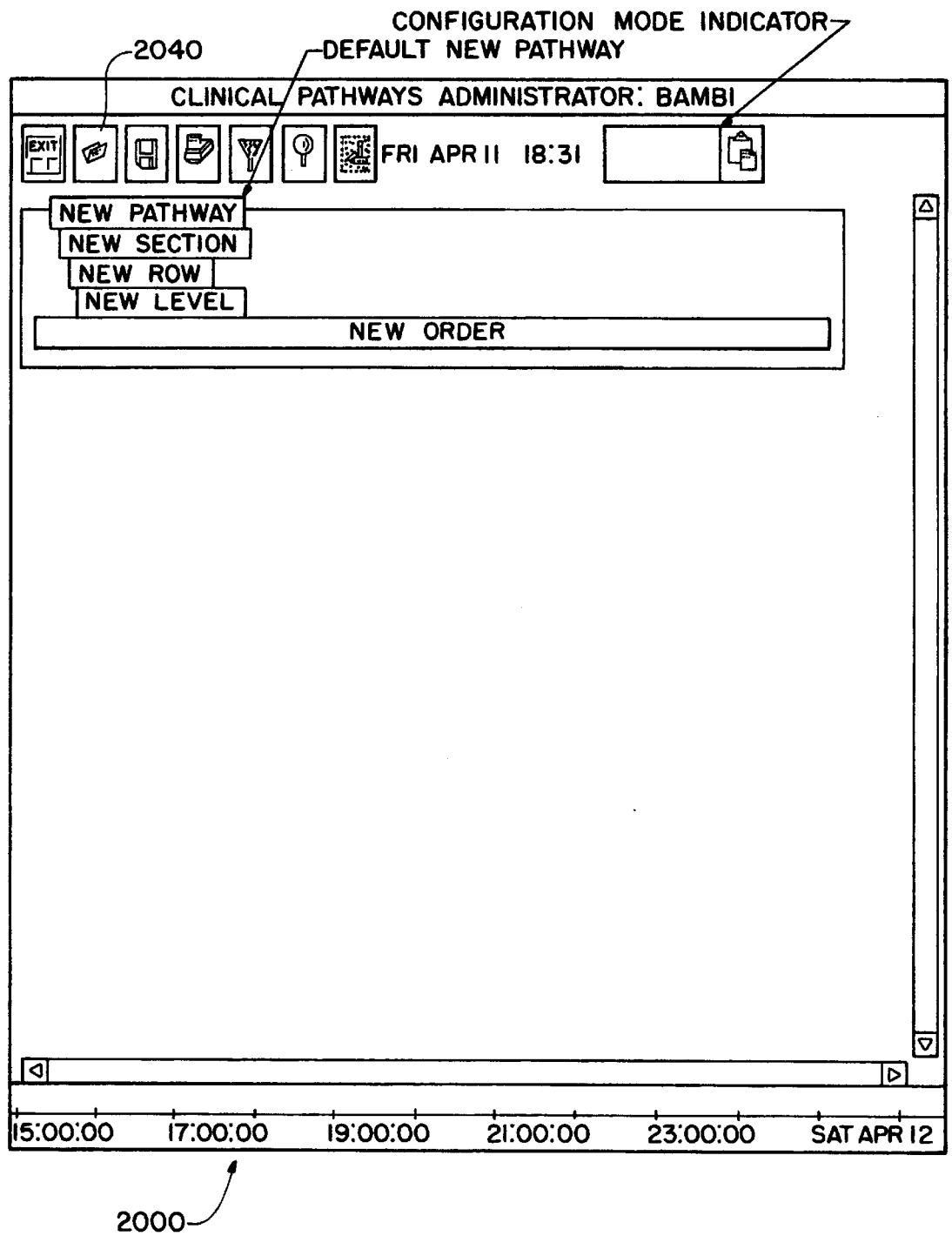
FIG. 20 is a clinical pathways administrator screen in a configuration mode with a default clinical pathway.

Considering now the configuration of the Clinical Pathways Administrator with regard to FIG. 20, the configuration mode is available for one user per environment.

A new Clinical Pathway can be created by: developing a clinical pathway from scratch; or copy an existing clinical pathway and modify it as needed.

Although the following instructions apply to creating a new clinical pathway, the functions are applicable to modifying an existing clinical pathway.

To change to the Configuration Mode to modify an existing template or create a new one, select the Clinical Pathway Administrator Screen. Click on the "Configuration Mode" icon. A User Verification window will appear. Enter in your ID code. Press the Enter key. The "Configuration Mode" indicator 2020 will appear in the middle, center of the screen.

To create a new clinical pathway, click on the "Open" icon 2040. The Current Pathways window will appear. Click on the "New Pathways" option. Click on the "OK" button. The template for the New Pathway will appear. Be sure and change the name of the template to a new name. When creating a new clinical pathway, it is recommended to configure the pathway with the referenced functions as shown in Table I.

TABLE I

| Step | Action | Function |
|---|---|---|
| 1 | Edit the label of the Clinical Pathway | Editing the Name of an Item |
| 2 | Create the necessary Section items | Creating, Copying or Moving an Item |
| 3 | Edit the labels for the Section item | Editing the Name of an Item |
| 4 | Create the necessary Row item | Creating, Copying or Moving an Item |
| 5 | Edit the labels for the Row item | Editing the Name of an Item |
| 6 | Create the necessary Step item | Creating, Copying or Moving an Item |
| 7 | Edit the labels for the Step item | Editing the Name of an Item |
| 8 | Assign the outcome for each item | Assigning an Outcome to the Step |
| 9 | Assign the weight for each item | Editing the Name of an Item |
| 10 | Create orders | Adding a Future Order |
| 11 | Set the Start and Stop Times | Changing the Start Time for a Pathway, Section or Row |

A new item can be quickly created or moved by copying and pasting a similar item. An item with any subsets can be copied to create the new item. To create or move an item, move the cursor to the item to be copied or moved. Hold down the middle mouse button. The cursor will change to the Copy icon. The Copy icon will take on the color for that item.

To copy an item, drag the Copy icon to the desired item. For example, when creating a new Row, select the desired row, hold down the middle mouse and drag the Copy cursor to the Section item in which the new row will reside. The item can also be pasted on the Clipboard icon at the top of the screen. Release the middle mouse button. The item will appear under and at the end of the selected item (or in the Clipboard icon). Children items will not be visible and will need to be expanded.

When an item is deleted, the subset of elements within the item will also be removed. To remove an item off a clinical pathway template, move the cursor to the desired item. Hold down the right mouse button. Click on the Delete option. The item will be removed from the pathway. The Pathway Element cannot be deleted.

Figure 21:
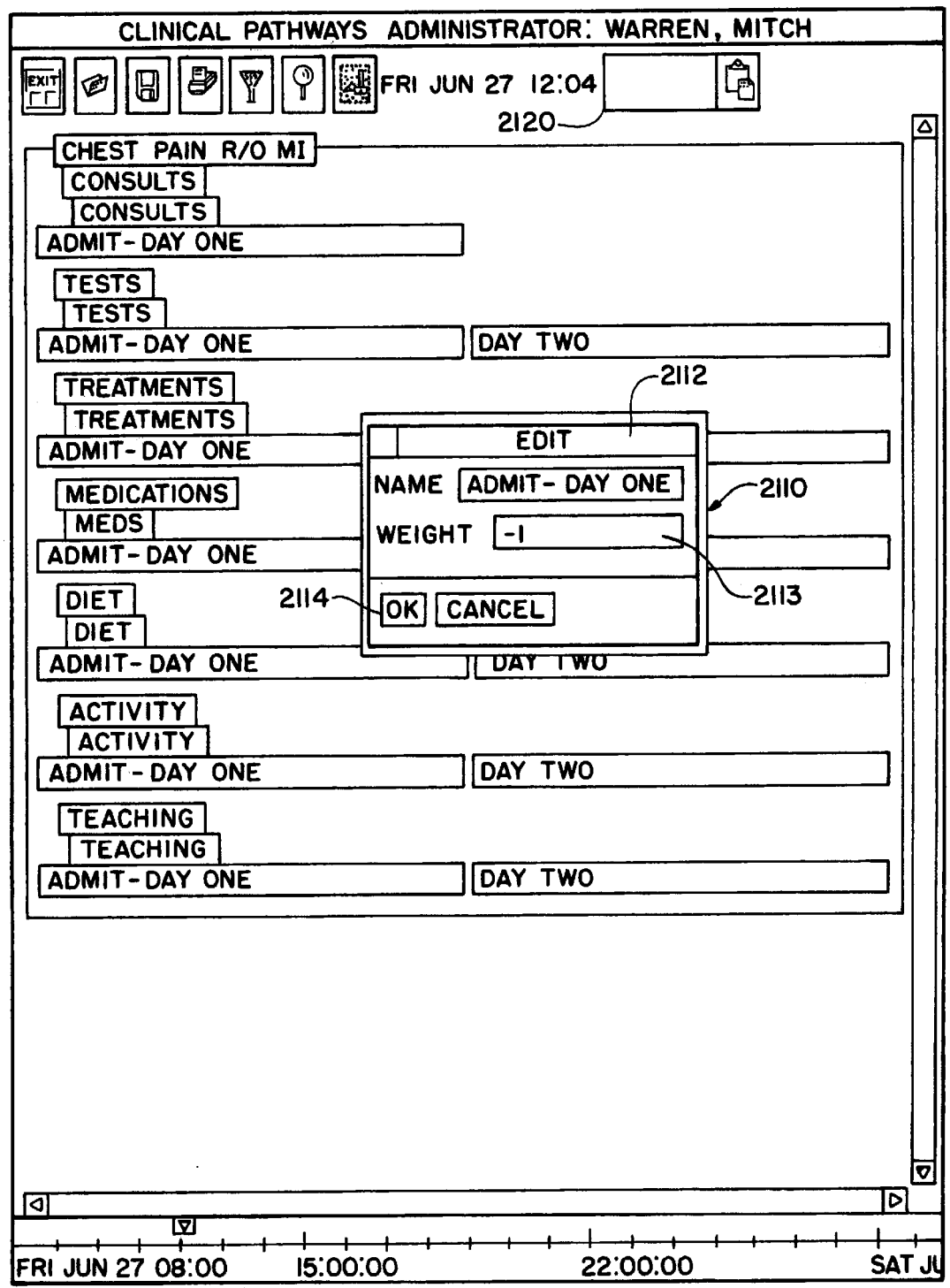
FIG. 21 is a clinical pathways administrator screen in the configuration mode with an edit name window.

To change the name of an item with reference to FIG. 21, move the cursor to the desired item. Hold down the right mouse button.

Click on the Edit Name/Weight option. The Edit window 2110 will appear. Click on the "Name" field 2112. Edit the text of the name. Click on the "OK" button 2114. The name of the item will appear as the edited text. The importance of an item in a clinical pathway can be assigned a weighted value based on a scale. The weight scale (e.g., 0–10) is defined by the hospital. This scale will then determine which items if changed will automatically generate a variance. To assign the importance of an item with a value, move the cursor to the desired item. Hold down the right mouse button.

Click on the Edit Name/Weight option. The Edit window 2110 will appear. Click on the "Weight" field 2113. Edit the weight in the Weight field. Click on the "OK" button 2114.

Orders cannot be assigned a weight.

To assign the Outcome for a Step, move the cursor to the Step. Hold down the right mouse button.

Figure 22:
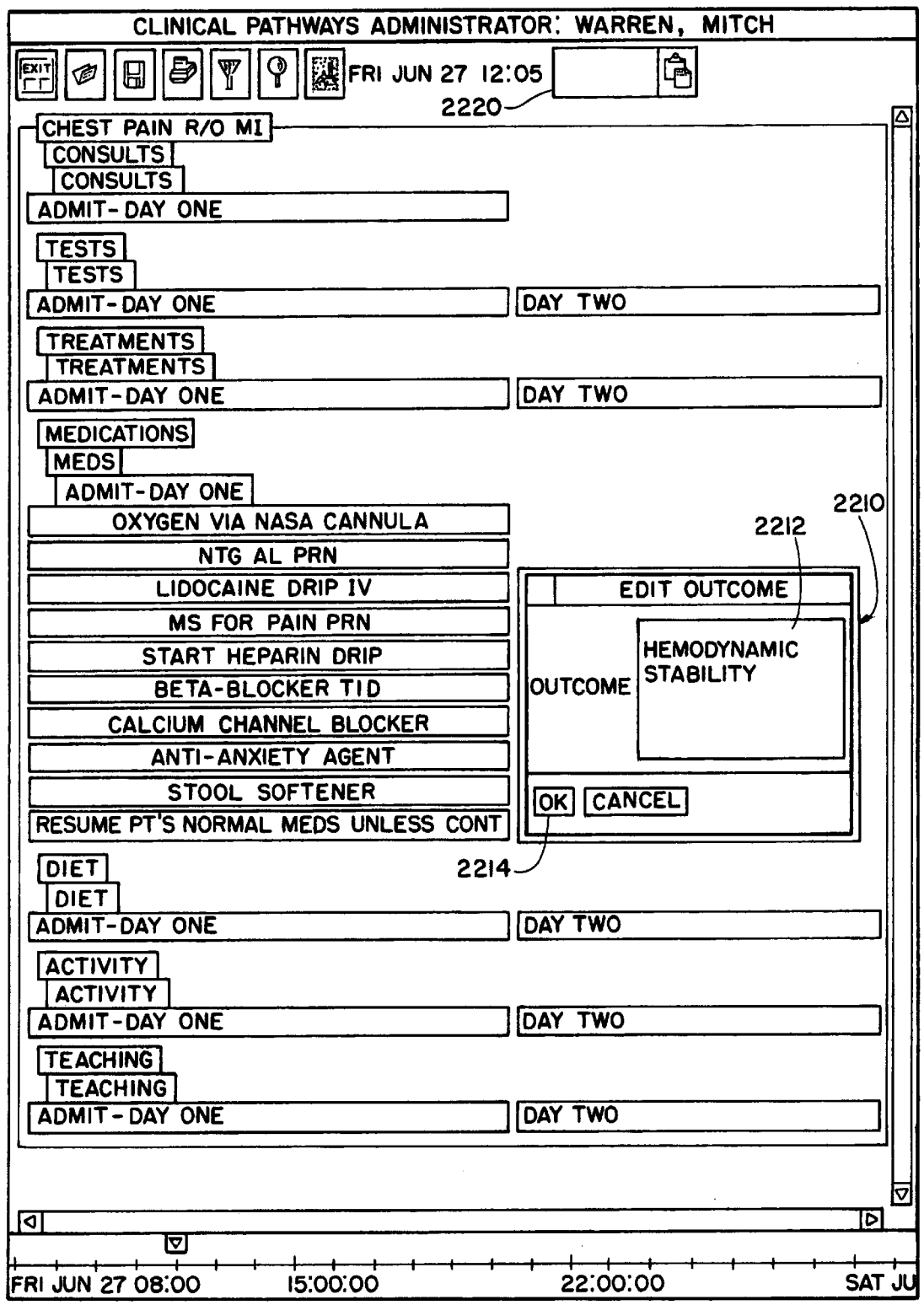
FIG. 22 is a clinical pathways administrator screen in the configuration mode with an edit outcome window.
Figure 23A:
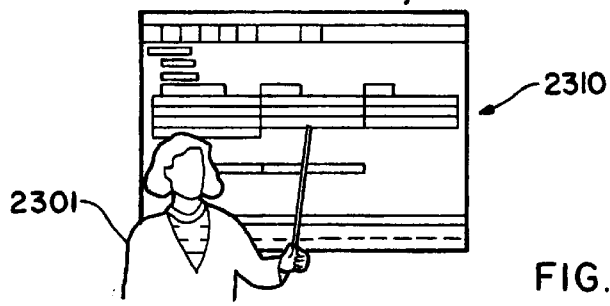
FIGS. 23A–23D is a graphical illustration of a charted variance in a time sequence.
Figure 23B:
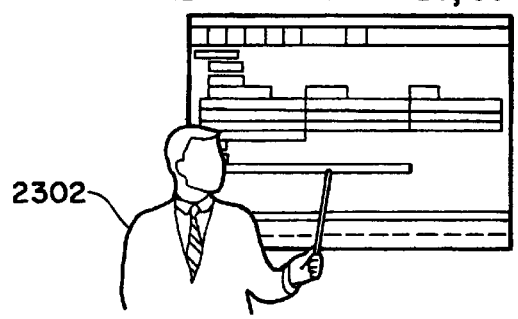
Figure 23C:
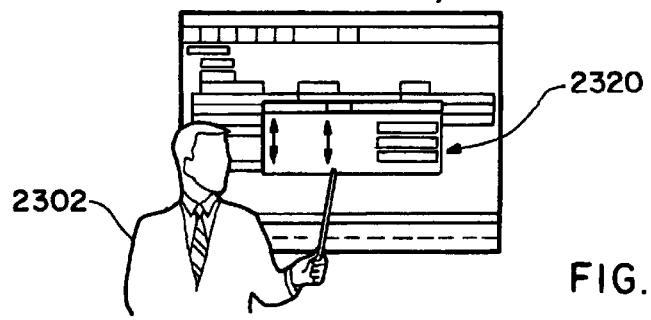
Figure 23D:
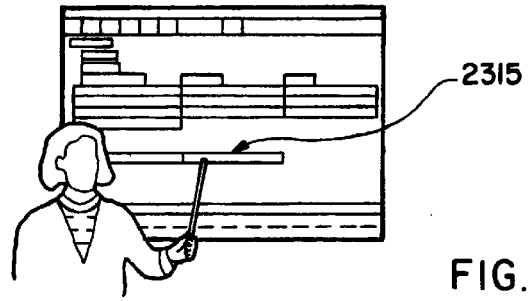

Click on the Edit Outcome option. The Edit Outcome window 2210 will appear as shown in FIG. 22. Type in the Outcome in the "Outcome" field 2212. Click on the "OK" button 2214.

To exit from the Configuration Mode and return to the Clinical Pathway Administration Screen, click on the "Configuration Mode" icon. The "Configuration Mode" indicator 2220 will no longer appear in the tool bar.

F. CONCURRENCY

As the CPA is a real-time application, it employs a concept of Concurrency. Concurrency allows multiple users to chart on the same clinical pathway and see each other's changes SIMULTANEOUSLY. For example, if one user on a clinical pathway charts a variance note for an order, then another user on the same pathway will see the order's variance symbol once the variance note is stored.

Concurrency Flow to the User

Referring now to FIGS. 23A–23D, the concept of concurrency employed by the CPA is shown in greater detail. If a Clinician 2301 (FIG. 23A) is viewing Patient Smith's Hip Replacement Pathway 2310 at the same time a Doctor 2302 (FIG. 23B) is, and the Doctor changes and stores the start time 2320 (FIG. 23C) for an order (which requires him to chart a variance note), the variance symbol 2315 ($) will appear on the order (FIG. 25D) to both the Clinician and the Doctor at the same time. The Clinician can then view the variance via the View Variance function.

The CPA is continuously 'refreshing' the screen and displaying all concurrent changes by multiple users. In addition, the order in which changes are recorded to the clinical pathway is the sequence in which they are stored. For example, if a User B (not shown) stores a change after a User A, (not shown) but before a User C, (not shown) then the changes to the clinical pathway are recorded as: Change by User A, Change by User B, and others.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A multiple user computerized clinical care system, comprising:

computer means for storing patient care information;

a group of terminal means coupled in communication with said computer means for sending patient information to said computer means for storage therein and for retrieving stored patient information therefrom so that health care providers can utilize the terminals to retrieve current patient information;

each one of said terminal means having means for generating patient information variance requests to cause selected portions of the patient information to be updated;

managing means for receiving temporarily and managing said patient information variance requests received from said terminals to facilitate modifying current patient information to update said patient care information;

said managing means including means for storing the received variance requests in the order in which the variance requests are received from said terminal means for a given patient, without denying at any time any terminal means access to the patient care information;

said managing means for selecting and sending simultaneously one of the stored patient information variance requests to all terminal means currently accessing the patient care information for said given patient in a concurrent manner to facilitate updating said patient care information for said given patient;

means for enabling the terminal means to receive the selected one of said variance requests substantially concurrently for said given patient, without causing any user to wait for the current variance information;

each one of said terminal means having means responsive to the received one of said variance requests for causing concurrently the accessed patient information for said given patient to be updated in accordance with the received one of said variance requests; and wherein no terminal means is locked for use at any time and no terminal means is ever denied access at any time to the patient care information, whereby all terminal means are updated substantially simultaneously.

2. A system according to claim 1, further including means for generation a variance indicia to indicate the occurrence of a stored variance information for a given patient;

means for sending said variance indicia to terminals monitoring patient information for the given patient to alert the users to the existence of variance.

3. A system according to claim 2, further including means for retrieving variance notes describing the variance.

4. A system according to claim 3, wherein said means for managing includes means for generating a list of variances and means for sending said list to said terminals upon request by the users.

5. A system according to claim 3, further including network means for interconnecting said computer means and said group of terminal means in communication with one another.

6. A system according to claim 1, wherein said patient information is encapsulated within an object.

7. A method of using a multiple user computerized clinical care system, comprising:

storing patient care information in a computer means and retrieving the stored patient care information therefrom so that health care providers can utilize terminal means to retrieve current patient information at any time so that the patient care information is always accessible to the terminal means;

generating at the terminal means patient information variance requests indicative of requested modifications to selected portions of the patient care information;

receiving with the use of managing means the patient information variance requests received from the terminal means to modify the current patient information and permit the terminal means to access the current patient information at any time without any lockout delay;

storing temporarily in the managing means the variance information in the order in which the variance requests are received for a given patient;

selecting with the use of the managing means one of the stored variance requests;

sending simultaneously with the use of the managing means the selected variance request to all of the terminal means currently accessing the patient care information for the given patient to facilitate the updating of the patient care information in a concurrent manner;

enabling the terminal means to receive the selected one of the variance requests for a given patient substantially concurrently for said given patient, without causing any user to wait for the current variance information;

causing concurrently the accessed patient information for said given patient to be updated in each terminal means in accordance with the received one of said variance requests; and wherein no terminal means is locked for use at any time and no terminal means is ever denied access at any time to the patient care information, whereby all terminal means are updated substantially simultaneously.

8. A method according to claim 7, further including generating a variance indicia to indicate the occurrence of a stored variance information for a given patient; and sending said variance indicia to a plurality of terminals monitoring patient information for the given patient to alert the users to the existence of the variances.

9. A method according to claim 8, further including retrieving variance notes describing the variance.

10. A method according to claim 9, wherein said managing includes generating a list of variances, and sending said list to said terminals upon request by the users.

11. A method according to claim 7 further including encapsulating said patient information variance in an object.

12. A method of using a clinical care system, the system having a plurality of terminal means for accessing patient care information, comprising:

storing a list of the terminal means currently accessing the patient care information;

receiving variance requests to the patient care information from one or more terminal means;

storing the received variance request in a given order;

selecting one of the stored variance requests;

sending the selected variance request to all the terminal means corresponding to the list of terminal means currently accessing patient care information;

receiving at all the terminal means substantially simultaneously the selected one of the variance requests;

causing concurrently the accessed patient information to be updated in each terminal means in accordance with the selected variance request; and wherein no terminal means is locked for use at any time and no terminal means is ever denied access at any time to the patient care information, whereby all terminal means are updated substantially simultaneously.

13. The method according to claim 12, wherein the selected variance request includes an inverse variance instruction sufficient to undo the current patient care information to facilitate rendering effective the selected variance request.

14. The method according to claim 12, wherein the selected variance request is an object.

15. The method according to claim 12, further comprising storing an action list indicative of the received variance requests.

16. The method according to claim 12, wherein the given order is on a first come, first served basis so that an earlier received variance request is acted upon before any later received variance request.

17. The method according to claim 12, wherein the patient care information is stored in a central storage means.

18. A clinical care system having a plurality of terminal means for accessing patient care information, comprising:

means for storing a list of the terminal means currently accessing the patient care information;

means for receiving variance requests to the patient care information from one or more terminal means;

means for storing the selected variance request in a given order;

means for selecting one of the stored variance requests;

means for sending the selected variance request to all the terminal means on the list of terminal means currently accessing patient care information;

means for receiving at all the terminal means substantially simultaneously the selected one of the variance requests;

means for causing concurrently the accessed patient information to be updated in each terminal means in accordance with the selected variance request; and wherein no terminal means is locked for use at any time and no terminal means is ever denied access at any time to the patient care information, whereby all terminal means are updated substantially simultaneously.

19. The clinical care system according to claim 18, wherein the selected variance request includes an inverse variance instruction sufficient to undo the current patient care information to facilitate rendering effective the selected variance request.

20. The clinical care system according to claim 18, wherein the selected variance request is an object.

21. The clinical care system according to claim 18, further comprising means for storing an action list indicative of the received variance requests.

22. The clinical care system according to claim 18, wherein the given order is on a first come, first served basis so that an earlier received variance request is acted upon before any later received variance request.

23. The clinical care system according to claim 18, further comprising central storage means for storing the patient care information.

* * * * *